United States Patent
Herring

(10) Patent No.: US 11,975,990 B2
(45) Date of Patent: May 7, 2024

(54) PHOTOREACTOR AND FORMULATIONS FOR ENVIRONMENTAL REMEDIATION AND METHODS OF USE THEREOF

(71) Applicant: Rodney Herring, Victoria (CA)

(72) Inventor: Rodney Herring, Victoria (CA)

(*) Notice: Subject to any disclaimer, the term of this patent is extended or adjusted under 35 U.S.C. 154(b) by 437 days.

(21) Appl. No.: 17/428,259

(22) PCT Filed: Feb. 4, 2020

(86) PCT No.: PCT/CA2020/000011
§ 371 (c)(1),
(2) Date: Aug. 3, 2021

(87) PCT Pub. No.: WO2020/160638
PCT Pub. Date: Aug. 13, 2020

(65) Prior Publication Data
US 2022/0169537 A1 Jun. 2, 2022

(51) Int. Cl.
*C02F 1/30* (2023.01)
*A61L 9/18* (2006.01)
(Continued)

(52) U.S. Cl.
CPC ...... *C02F 1/30* (2013.01); *A61L 9/18* (2013.01); *C02F 1/001* (2013.01); *C02F 1/725* (2013.01);
(Continued)

(58) Field of Classification Search
CPC .. A61L 2/088; A61L 9/18; A61L 9/205; A61L 2202/11; A61L 2209/14;
(Continued)

(56) References Cited

U.S. PATENT DOCUMENTS

| 10,413,888 B2 | 9/2019 | Herring |
| 2005/0208343 A1 | 9/2005 | Kim |

(Continued)

FOREIGN PATENT DOCUMENTS

| EP | 0827229 | 3/1998 |
| JP | 2008093549 | 4/2008 |

(Continued)

OTHER PUBLICATIONS

JP2008093549A—EPO Machine Translation (Year: 2023).*

(Continued)

*Primary Examiner* — Patrick Orme
(74) *Attorney, Agent, or Firm* — Baumgartner Patent Law, LLC; Marc Baumgartner

(57) ABSTRACT

A non-biological, visible light photoreactor is provided, the photoreactor comprising: a fiberglass sheet, which includes fibers and interstitial spaces between the fibers; and a low iron oxide content, iron-doped titanium dioxide film on the fibers, the film containing about 0.5 atomic percent iron and an iron oxide content of less than about 0.075 atomic percent iron. The photoreactor may be configured as a tube with a light emitting diode housed therein, a cap at one end of the tube that has inlets to accept pressurized air and a plate at the other end of the tube, such that the air is forced through the photoreactor.

16 Claims, 16 Drawing Sheets

(51) Int. Cl.
*C02F 1/00* (2023.01)
*C02F 1/72* (2023.01)
*C02F 101/30* (2006.01)

(52) U.S. Cl.
CPC ....... *A61L 2209/14* (2013.01); *A61L 2209/21* (2013.01); *C02F 2101/30* (2013.01); *C02F 2305/10* (2013.01); *C02F 2307/02* (2013.01)

(58) Field of Classification Search
CPC ........ A61L 2209/21; C02F 1/001; C02F 1/30; C02F 1/725; C02F 2101/30; C02F 2305/10; C02F 2307/02; C01G 23/047
See application file for complete search history.

(56) References Cited

U.S. PATENT DOCUMENTS

| | | | |
|---|---|---|---|
| 2009/0301859 | A1 | 12/2009 | Sahle-Demessie |
| 2010/0294727 | A1 | 11/2010 | Gilbeau |
| 2015/0068906 | A1 | 3/2015 | Curran |

FOREIGN PATENT DOCUMENTS

| | | | | | |
|---|---|---|---|---|---|
| JP | 2008093549 | A | * | 4/2008 | |
| KR | 101862989 | B1 | * | 5/2018 | |
| WO | WO-2008001405 | A2 | * | 1/2008 | ............. B01D 39/12 |
| WO | 2018064747 | | | 4/2018 | |
| WO | WO-2018064747 | A1 | * | 4/2018 | ............ B01J 21/063 |

OTHER PUBLICATIONS

KR101862989B1—EPO Machine Translation (Year: 2023).*
International Search Report for PCT/CA2019/000130, mailed May 7, 2020, 3 pages.
Written Opinion of the International Searching Authority for PCT/CA2020/000011, mailed May 7, 2020, 7 pages.
"Nano Anti-Microbial Solution" retrieved from http://www.mchnanosolutions.com/.
Moradi, V. et al., "Significant improvement in visible light photocatalytic activity of Fe doped Ti02 using an acid treatment process." Applied Surface Science 427, 791-799, Jan. 1, 2018 (Jan. 1, 2018).

* cited by examiner

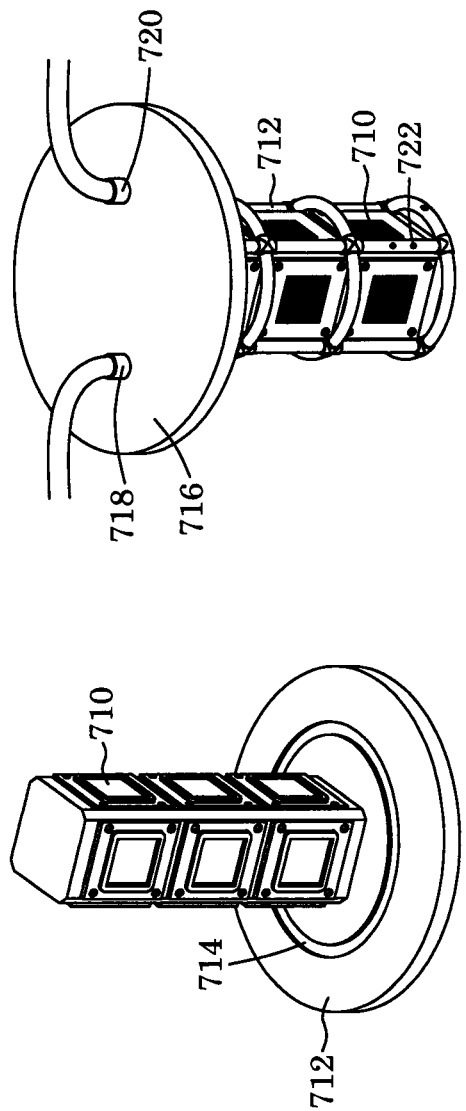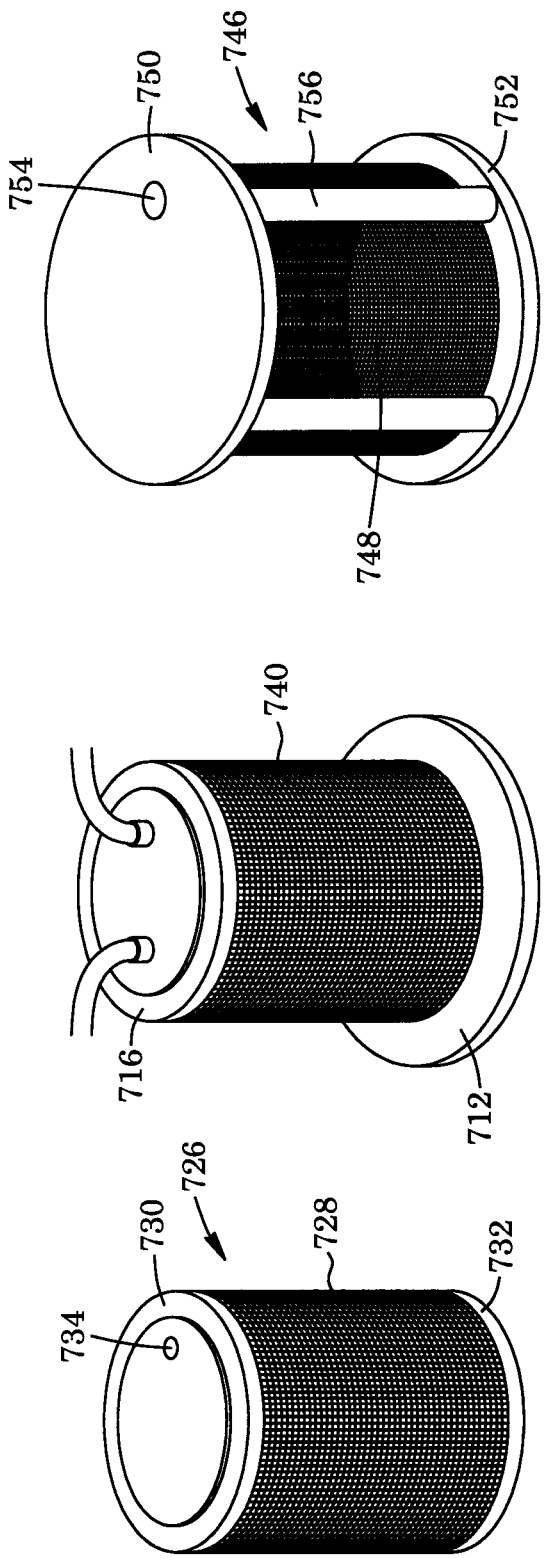
FIG. 17A
FIG. 17B
FIG. 17C
FIG. 17D
FIG. 17E

PHOTOREACTOR AND FORMULATIONS FOR ENVIRONMENTAL REMEDIATION AND METHODS OF USE THEREOF

CROSS REFERENCE TO RELATED APPLICATIONS

This application is the U.S. national phase of International Application No. PCT/CA2020/000011, filed Feb. 4, 2020, which claims priority to Canadian Patent Application Serial No. 3,033,255, filed 4 Feb. 2019, both entitled PHOTOREACTOR AND FORMULATIONS FOR ENVIRONMENTAL REMEDIATION AND METHODS OF USE THEREOF. The above-identified priority patent applications are incorporated herein by reference in their entirety.

FIELD

The present technology is directed to the use of low iron oxide content, iron-doped titanium dioxide as a non-biological, visible light photoreactor. More specifically, it is directed to apparatus or formulations that include nanoparticles of low iron oxide content, iron-doped titanium dioxide.

BACKGROUND

United States Patent Application 20150068906 discloses a photocatalyst and a method of manufacturing a photocatalyst. More specifically, the present invention relates to a high surface area TiO2 photocatalyst formed by electrolytic discharge oxidation (EDO) of a substrate comprising titanium. A flexible high surface area photocatalyst architecture comprising a compliant, cohesive, well-adhered and highly porous surface layer of the anatase phase of titanium dioxide is provided. The highly porous surface layer of the anatase phase of titanium dioxide is formed in a single step by the electrolytic oxidation of a titanium surface on a permeable, flexible, and electrically conductive substrate sponge structure.

Waste water treatment using $TiO_2$ as a photocatalyst has attracted a great deal of attention because of its high activity, chemical stability, robustness against photo-corrosion, low toxicity, low pollution load, and availability at low cost. However, the shortcomings of conventional powder catalysts include low efficiency of light use, difficulty of stirring during reaction and separation after reaction (usually using ultra-filtration), and low-concentration contamination near $TiO_2$ due to its low surface area.

United States Patent Application 20090301859 discloses that a reactor produces a surface corona for emitting UV light and for the production of ozone by passing air or oxygen through the surface corona. The emitted UV light activates a photocatalyst coated on a surface facing a surface with embedded electrodes which generate the surface corona. The photocatalyst is a thin film of nanoparticle $TiO_2$ with primary particle size of 0.02 to 0.2 .mu.m was deposited on a substrate by a flame aerosol method. The method combines ozonation and photocatalysis to provide effective and efficient oxidation of alcohols and hydrocarbons to value added products. The method can also be used for air and water cleaning.

The current methods used to perform $TiO_2$ photocatalysis also include the application of UV onto a $TiO_2$ surface coating in the presence of the target waste stream. There are three possible serious drawbacks of UV/$TiO_2$ photocatalysis technology that has resulted in the failure of the technology to become established as a successful industrial waste water treatment technology. Firstly, the ability of the UV to effectively penetrate waste stream which could be turbid, secondly the limited effect of the $TiO_2$ catalyst due to the relatively small surface reaction area used in current systems, and thirdly UV has harmful effects on microbes. These drawbacks of $TiO_2$ result in low efficiency of photocatalytic activity in practical applications.

www.mchnanosolutions.com discloses the use of titanium dioxide for cleaning surfaces and decontamination of liquids. Their system is reliant upon ultraviolet (UV) light, which is expensive and which does not penetrate glass.

Microbial fuel cells (MFCs) are becoming an attractive method for treatment of wastewater because they enable energy recovery and reduction of production of excess sludge. However, the use of proton exchange membranes (PEMs) and mediators limit the application of MFCs for treatment of wastewater. Transfer of protons through PEMs is difficult since PEMs get fouled due to suspended solids and soluble contaminants found in wastewater. Moreover, PEMs are expensive.

Although the performance of MFCs has improved significantly in recently years, it is still much lower than that of chemical fuel cells. It was found that the cathodic losses, especially the cathodic activation losses, were one of the most important factors influencing the MFC performance. At research level significant progress has been made in advancing the fundamental science for MFCs, achieving power densities approaching those suitable for practical application (>1 $kW/m^3$). However, such laboratory MFCs have a number of important limitations that prevent commercial application:

(1) existing MFC designs utilize expensive platinum catalysts and proton/cationic exchange membranes that are not commercially viable for industrial scale wastewater treatment processes;

(2) exoelectrogen microbes have a broad but limited metabolic range and thus some organic species are not degraded during treatment. Existing MFCs typically achieve <80% COD reduction, and thus demonstrate inferior treatment performance (COD reduction) to aerobic processes, thereby negating the benefits achieved for energy production; and do not enable water re-use for on-site non-potable applications; and do not fully utilize the inherent energy content of the wastewater (low coulombic efficiency); and (3) MFC treatment systems are still to be demonstrated at pilot scale, limited mainly by the lack of scalable and commercially viable MFC designs.

EP 0 827 229 discloses a biofuel cell which can react with an electrode without a mediator. Graphite rods are used as electrodes, and the anode and cathode compartments are separated by a sintered glass. Alternatively, the electrodes may be formed from graphite felt and separated by a cation-exchange membrane.

US 20050208343 discloses a mediator-less microbial fuel cell comprising a cathode compartment and an anode compartment which are separated with glass wool or glass beads, means for feeding air to the cathode compartment and means for feeding wastewater to the anode compartment. Graphite felt (which may be coated with a metal such as platinum) is used as an electrode of the cathode compartment.

United States Patent Application 20100294727 discloses a process for degrading organic substances in an aqueous composition comprising a step (a) wherein, in a liquid reaction medium, said aqueous composition is reacted with at least one composition comprising hydroxide ions (OH.sup.-) and hypochlorite in a molar ratio between hydroxide and hypochlorite higher than or equal to 0.001 and lower than 1.5, in order to oxidize said organic substances. Hypochlorite is a toxic chemical and therefore should not be used in cleaning contaminated water.

The use of iron-doped titanium dioxide in wastewater remediation is disclosed in WO2018064747, which is directed to a method of making a visible light photo-catalyst, the method comprising doping a titanium dioxide nanocrystal with iron to provide an iron-doped nanocrystal, washing the iron-doped nanocrystal with an acid to produce an acid-washed iron-doped titanium dioxide nanocrystal and rinsing the acid-washed iron-doped titanium dioxide nanocrystal to remove a residual of the acid, thereby providing a visible light photo-catalyst.

What is needed is a non-microbial, high efficiency photoreactor for remediation of fluids such as wastewater and air. It would be preferable if it utilized visible light. It would be preferable if the photoreactor iron-doped titanium dioxide with a surface having a low iron oxide content. It would be preferable if the iron-doped titanium dioxide functionalizes a filter, which would preferably be poly-paraphenylene terephthalamide fabric, carbon fiber fabric, fiberglass fabric or sintered glass. Alternatively, the iron-doped titanium dioxide would be provided in a liquid. It would be most preferable if the iron-doped titanium dioxide had a surface that was substantially free of iron oxide.

SUMMARY

The present technology is a non-microbial, visible light photoreactor for remediation of fluids such as wastewater and air. It is a high efficiency photoreactor. The photoreactor includes iron-doped titanium dioxide with a surface having a low iron oxide content. The iron-doped titanium dioxide functionalizes a filter, which is preferably poly-paraphenylene terephthalamide fabric, carbon fiber fabric, fiberglass fabric or sintered glass. Alternatively, the iron-doped titanium dioxide is provided in a liquid. It is most preferable that the iron-doped titanium dioxide has a surface that is substantially free of iron oxide.

In one embodiment, a non-biological, visible light photoreactor is provided, the photoreactor comprising: a porous glass, carbon fiber or poly-paraphenylene terephthalamide filter, which includes fibers and interstitial spaces between the fibers; and an iron-doped titanium dioxide film on the fibers, the film including a surface with a low iron oxide content.

In the photoreactor, the surface may be substantially iron oxide free.

In the photoreactor, the porous glass, carbon fiber or poly-paraphenylene terephthalamide filter may be retained by a frame, the frame comprising a cap, a plate and support members, the support members attached to the cap and the plate and extending therebetween.

The photoreactor may further comprise a plurality of visible light emitting diodes housed in the frame.

In the photoreactor, the film may include about 0.1 atomic % iron to about 2.0 atomic % iron.

The photoreactor may further comprise: an anode which is a metal mesh; a cathode which is a metal mesh, the anode and the cathode sandwiching the filter; and electrical connectors for the anode and the cathode.

The photoreactor may further comprise at least one air line which include apertures, the air line located proximate the filter; and an air inlet in fluid communication with the air line.

The photoreactor may further comprise a heater which is proximate the cap or the plate.

In the photoreactor, there may be a plurality of filter layers and an outermost filter layer may include a discontinuous layer of gold.

In the photoreactor, the porous glass, carbon fiber or poly-paraphenylene terephthalamide filter may be formed into at least one porous tube which defines a bore.

In the photoreactor, the plurality of visible light emitting diodes may be housed in the bore within the frame.

In the photoreactor, the anode and the cathode may be tubular, extend between the cap and the plate and sandwich the porous tube.

In the photoreactor, the air lines may be located proximate the porous tube.

The photoreactor may further comprise a heater which is proximate the cap or the plate.

In the photoreactor, there may be a plurality of porous tube layers and an outermost layer includes a layer of gold.

In the photoreactor, the layer of gold may be a discontinuous layer of gold and the outermost layer further includes the iron-doped titanium dioxide film.

In another embodiment, a non-biological, visible light photoreactor is provided, the photoreactor comprising: a porous glass, carbon fiber or poly-paraphenylene terephthalamide filter, which includes fibers and interstitial spaces between the fibers; a discontinuous layer of gold on the fibers; and an iron-doped titanium dioxide film on the fibers, the film including a surface with a low iron oxide content.

In the photoreactor, the film may include about 0.1 atomic % iron to about 2.0 atomic % iron.

In the photoreactor, the surface may be substantially iron oxide free.

In yet another embodiment, a method of non-biologically reducing organic waste in a fluid is provided, the method comprising: selecting a porous glass, carbon fiber or poly-paraphenylene terephthalamide filter, which includes fibers and interstitial spaces between the fibers, a discontinuous layer of gold on the fibers and an iron-doped titanium dioxide film on the fibers, the film containing about 0.5 atomic percent iron and including a surface with a low iron oxide content; exposing the filter to visible light; and concomitantly exposing the fluid to the filter.

In the method, the surface of the film may be substantially iron oxide free.

In the method, the exposing may be flowing the fluid through the filter.

In the method, the fluid may be air.

In the method, the fluid may be a liquid.

In the method, the liquid may be water.

In another embodiment, a non-biological, visible light photoreactor is provided, the photoreactor comprising: a porous glass, carbon fiber or poly-paraphenylene terephthalamide porous tube, which defines a bore and includes fibers and interstitial spaces between the fibers; an iron-doped titanium dioxide film on the fibers, the film including a surface which is substantially iron oxide free; a cap at a first end of the tube; a plate at a second end of the tube; a plurality of support members, the support members attached to the cap and the plate and extending therebetween; a plurality of visible light emitting diodes housed in the bore; an anode which is a metal mesh tube; and a cathode which is a metal mesh tube, the anode and the cathode extending between the cap and the plate and sandwiching the porous tube.

In the photoreactor, an outermost porous tube may include a layer of gold.

In the photoreactor, the layer of gold may be a discontinuous layer.

In the photoreactor, the film may include about 0.1 atomic % iron to about 2.0 atomic % iron.

FIGURES

FIG. 17A to E shows the components of the electro-visible light photo-chemical reactor from the inside to the outside. FIG. 17A shows the column of visible light LEDs; FIG. 17B shows the air lines; FIG. 17C shows the anode; FIG. 17D shows the mesh which has been gold coated and activated with the low iron oxide, iron-doped titanium dioxide particles; FIG. 17E shows the cathode.

Figure 18:
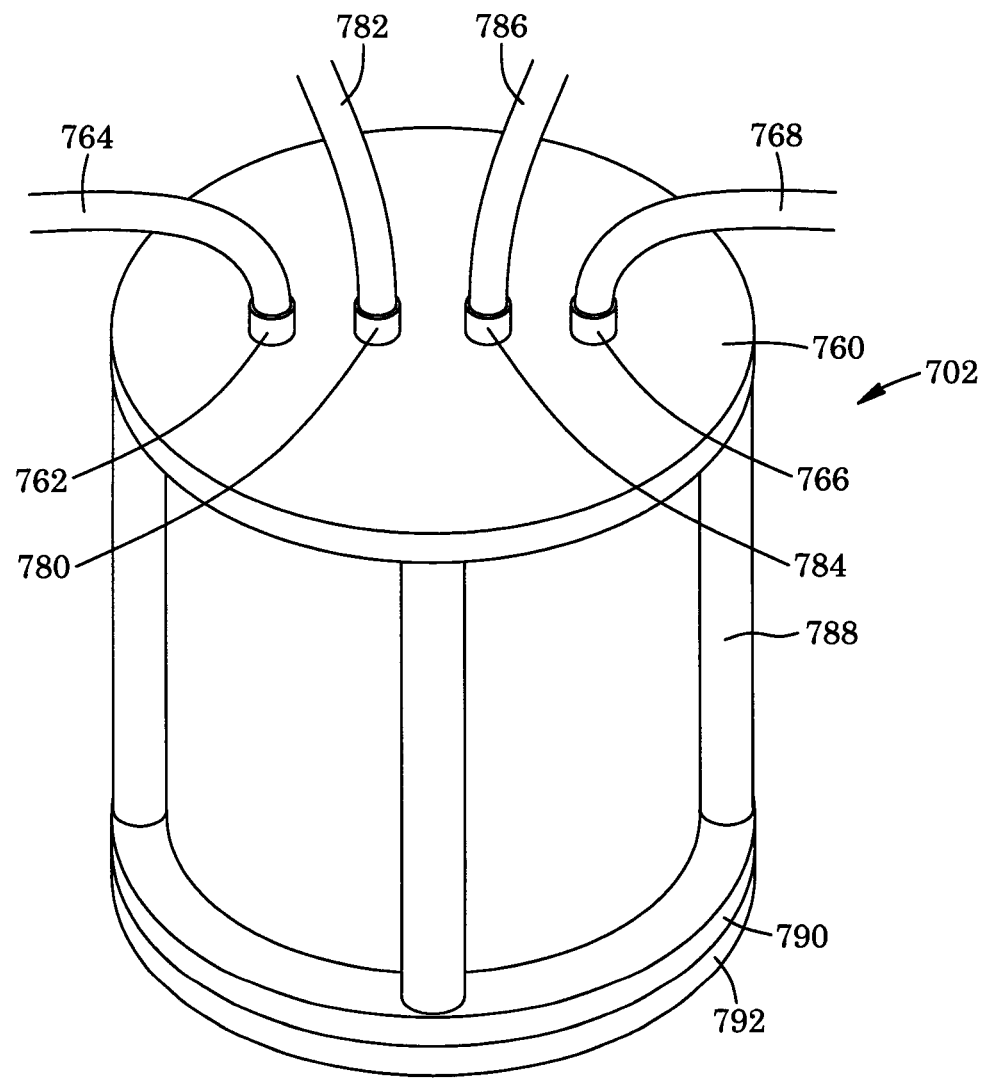

FIG. 18 is a perspective view of the assembled electro-visible light photo-chemical reactor.

Figure 19:
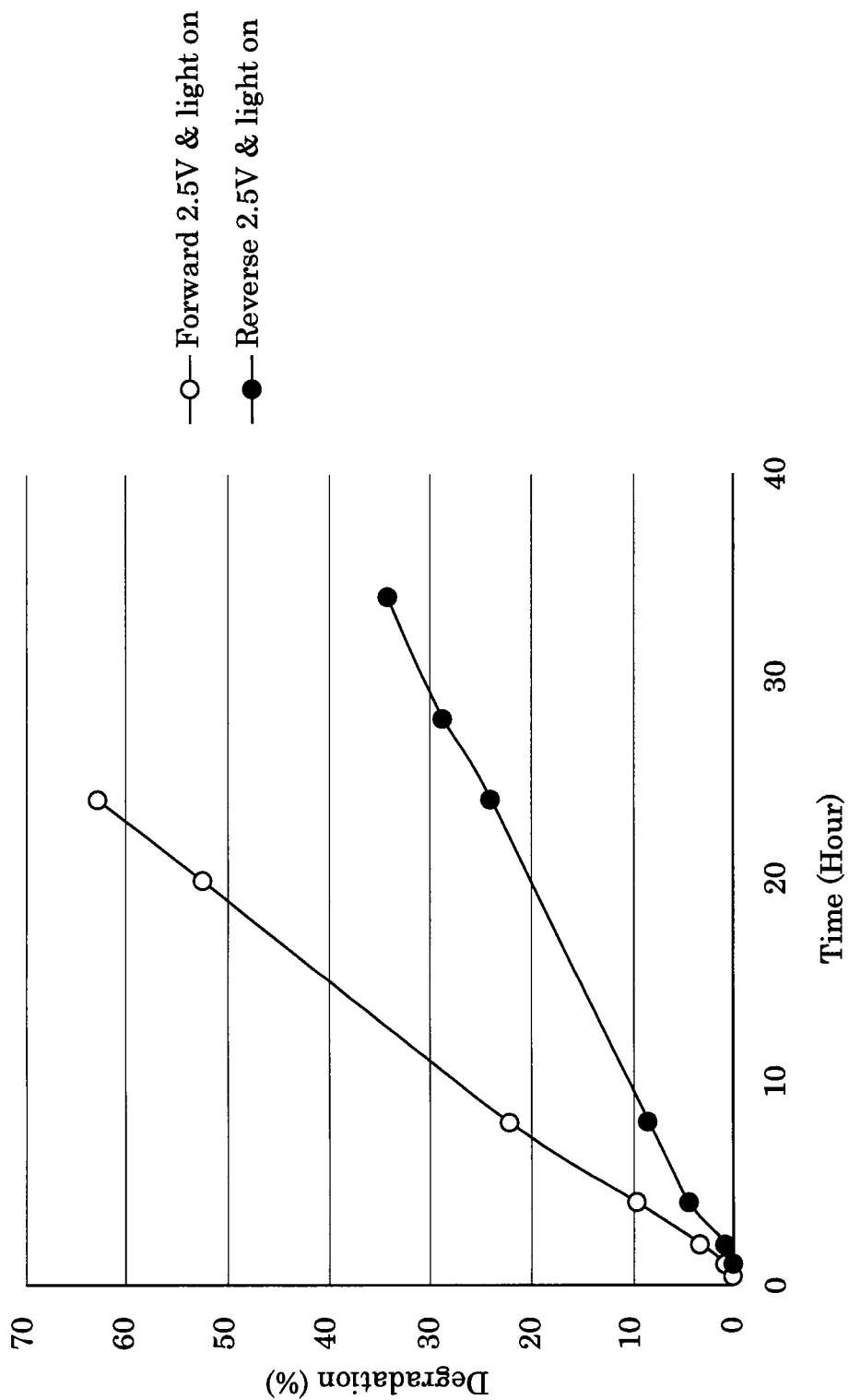

FIG. 19 is a graph showing the efficiency of cleaning wastewater when the cathode is on the air releasing side of the activated fiberglass sheets as compared to when the anode is on the air releasing side of the activated fiberglass sheets.

Figure 20:
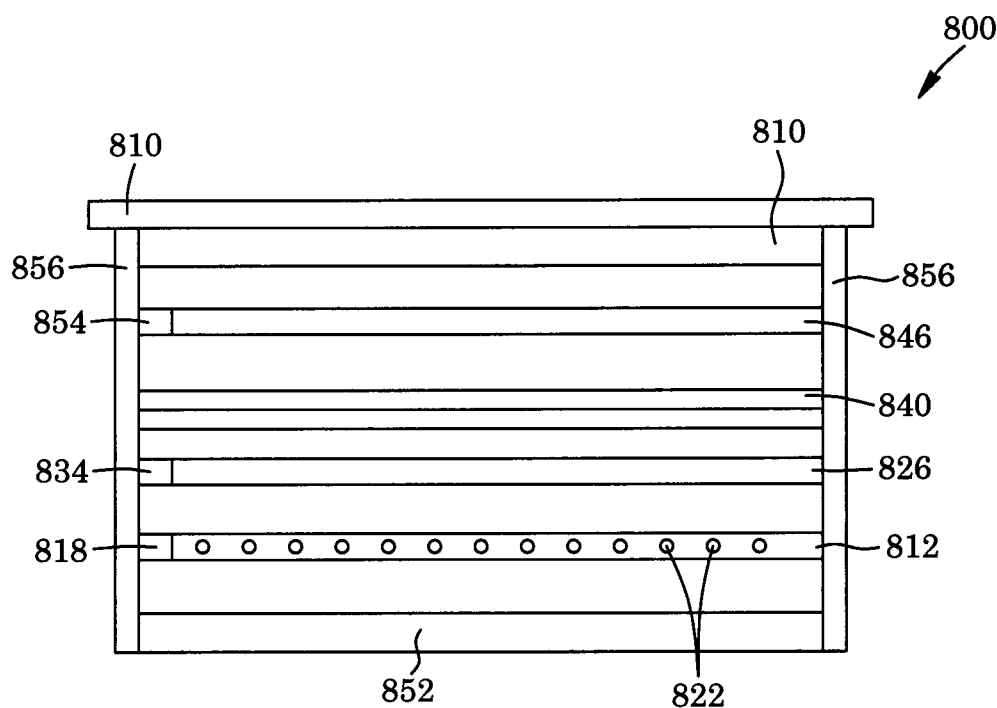

FIG. 20 is an exploded view of a planar electro-visible light photo-chemical reactor.

DESCRIPTION

Except as otherwise expressly provided, the following rules of interpretation apply to this specification: (a) all words used herein shall be construed to be of such gender or number (singular or plural) as the circumstances require; (b) the singular terms "a", "an", and "the", as used in the specification and the appended claims include plural references unless the context clearly dictates otherwise; (c) the antecedent term "about" applied to a recited range or value denotes an approximation within the deviation in the range or value known or expected in the art from the measurements method; (d) the words "herein", "hereby", "hereof", "hereto", "hereinbefore", and "hereinafter", and words of similar import, refer to this specification in its entirety and not to any particular paragraph, claim or other subdivision, unless otherwise specified; (e) descriptive headings are for convenience only and shall not control or affect the meaning or construction of any part of the specification; and (f) "or" and "any" are not exclusive and "include" and "including" are not limiting. Further, the terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the relevant art. Although any methods and materials similar or equivalent to those described herein can also be used, the acceptable methods and materials are now described.

Definitions

Physical vapour deposition—in the context of the present technology, physical vapour deposition includes, but is not limited to, magnetron sputtering, ion beam sputtering, reactive sputtering, ion assist deposition, high target utilization sputtering, pulsed laser deposition and gas flow sputtering.

Thin film—in the context of the present technology, a thin film is up to 5 microns in thickness. A film may be a partial coating, a deposit upon a surface, a complete coating or a plurality of layers. To be clear, gaps may occur where the surface below is exposed. It may be formed by, for example, but not limited to growing nanocrystals on the substrate, physical vapour deposition on the substrate or photolithography on the substrate.

Iron-doped titanium dioxide with a low iron oxide surface—in the context of the present technology, iron-doped titanium dioxide with a low iron oxide surface has about 0.1 atomic % iron to about 2.0 atomic % iron, preferably 0.25 atomic % iron to about 0.75 atomic % iron, and more preferably 0.5 atomic % iron and very small amounts of iron oxide on its surface (less than 5% of the surface being iron oxide) when viewed with X-ray photoelectron spectroscopy.

Substantially iron oxide free surface—in the context of the present technology, a substantially iron oxide free surface has an iron oxide content corresponding to less than about 0.001% atomic iron (less than 0.5% of the surface being iron oxide) when viewed with X-ray photoelectron spectroscopy.

Porous glass—in the context of the present technology, porous glass includes fiberglass, sintered glass and any glass formed by other means. The porous glass has interstitial spaces which can be as large as 40,000 square microns.

Fiberglass fabric—in the context of the present technology, fiberglass fabric is comprised of glass threads in a plain weave. It may have any thread count, for example, but not limited to 20×14 to 60×52, to 70×70 and may have a thickness, of, for example, but not limited to 3 μm 0.01 mm to 0.23 mm to 1 mm to about 5 mm, depending on the application. The thread count and the thickness of the threads determines the porosity of the end product.

Carbon fiber fabric—in the context of the present technology, carbon fiber fabric is very similar to fiberglass fabric in terms of the weave, the thread count and the thread thickness. The threads are made of long carbon fibers.

Kevlar®—in the context of the present technology, Kevlar is a fabric made from poly-paraphenylene terephthalamide threads. Poly-paraphenylene terephthalamide fabric is very similar to fiberglass fabric in terms of the weave, the thread count and the thread thickness.

Moist air—in the context of the present technology, moist air is defined as having a relative humidity of at least about 45%.

DETAILED DESCRIPTION

Figure 1B:
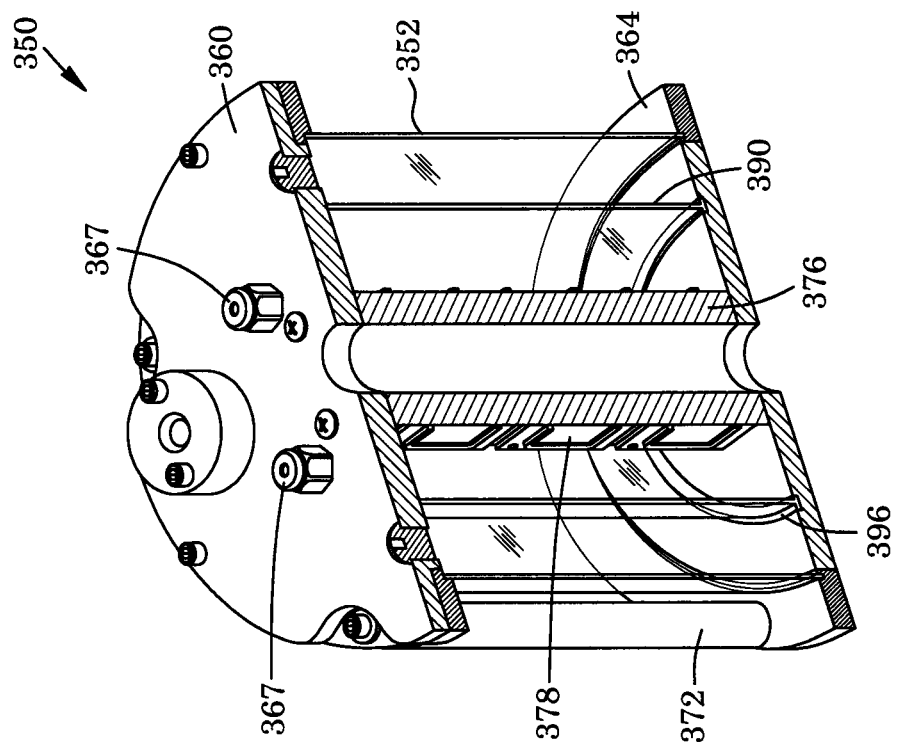
FIG. 1B is a medial sectional view of the photoreactor apparatus of FIG. 1A.
Figure 1A:
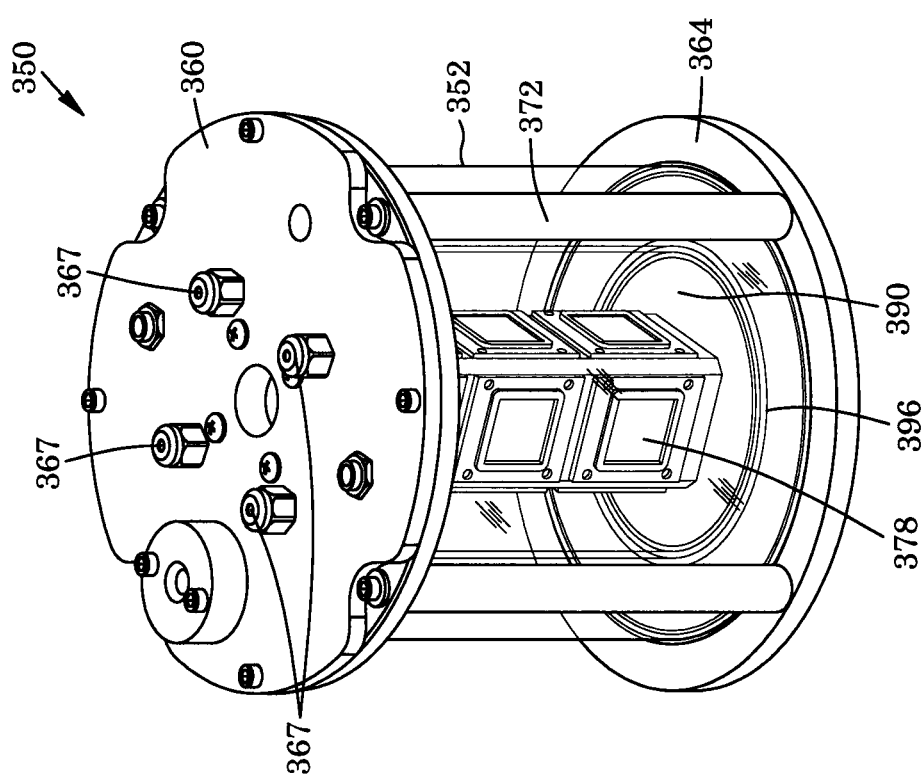
FIG. 1A is a perspective view of a photoreactor apparatus for cleaning wastewater.
Figure 11:
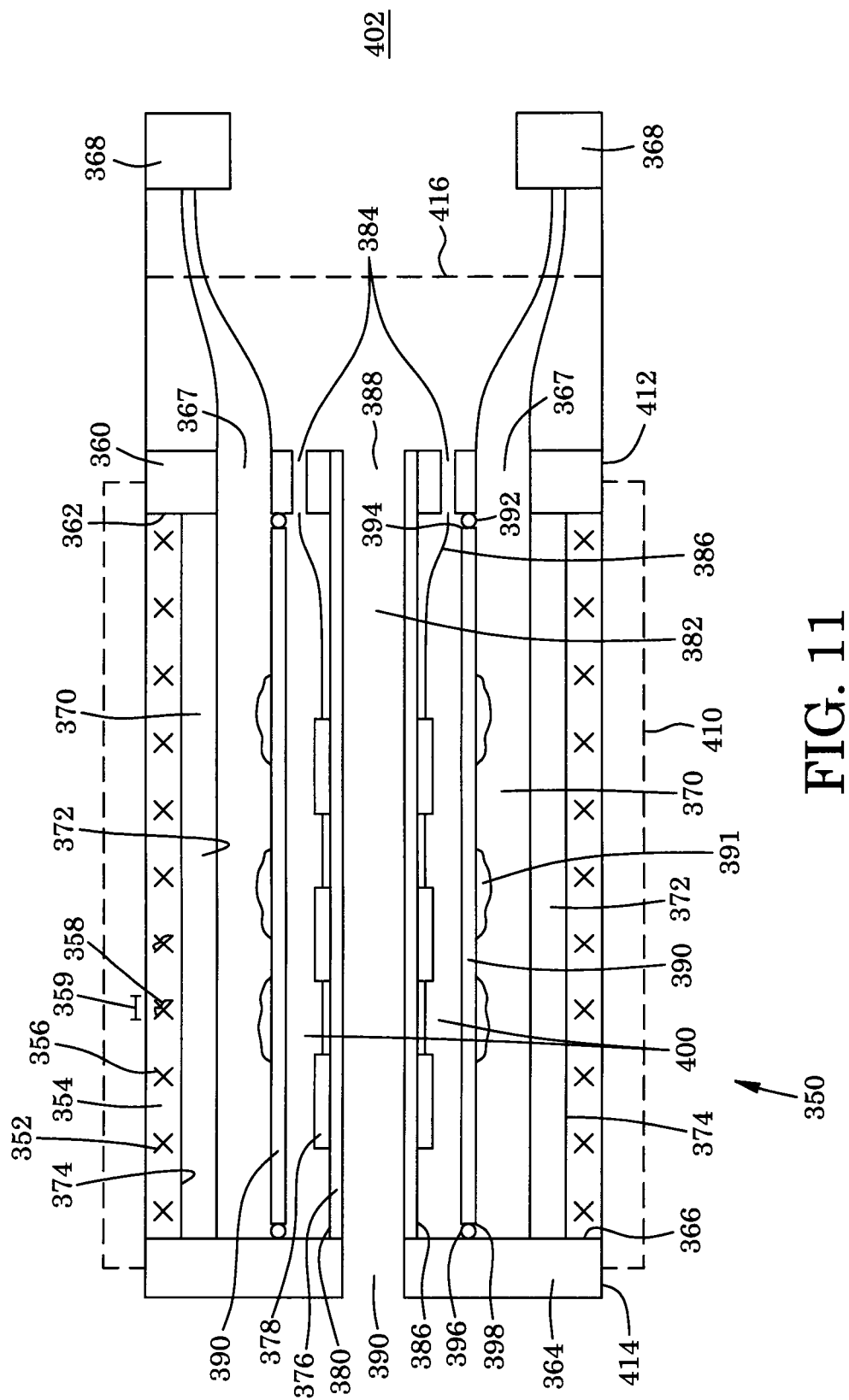
FIG. 11 is a schematic of a medial sectional view of the photoreactor apparatus of FIG. 1A for cleaning water.

An exemplary photoreactor apparatus 350 for cleaning contaminated liquids is shown in FIGS. 1A and 1B. It has an outer filter 352 that is functionalized with low iron oxide or substantially iron oxide free, iron-doped titanium dioxide. The filter 352 is supported by a cap 360 at one end, which has a plurality of apertures 367 and a plate 364 at the other end, with supports members 372 extending between the cap 360 and the plate 364. The cap 360, the plate 364 and the support members 372 form a frame. An inner tube 376 retains a plurality of light emitting diodes 378. A glass tube 390, which is also is functionalized with low iron oxide or substantially iron oxide, iron-doped titanium dioxide is located between the filter and the inner tube 376. A gasket 396 can be seen between the glass tube 390 and the plate 364. Details of this embodiment are shown in FIG. 11.

Figure 2:
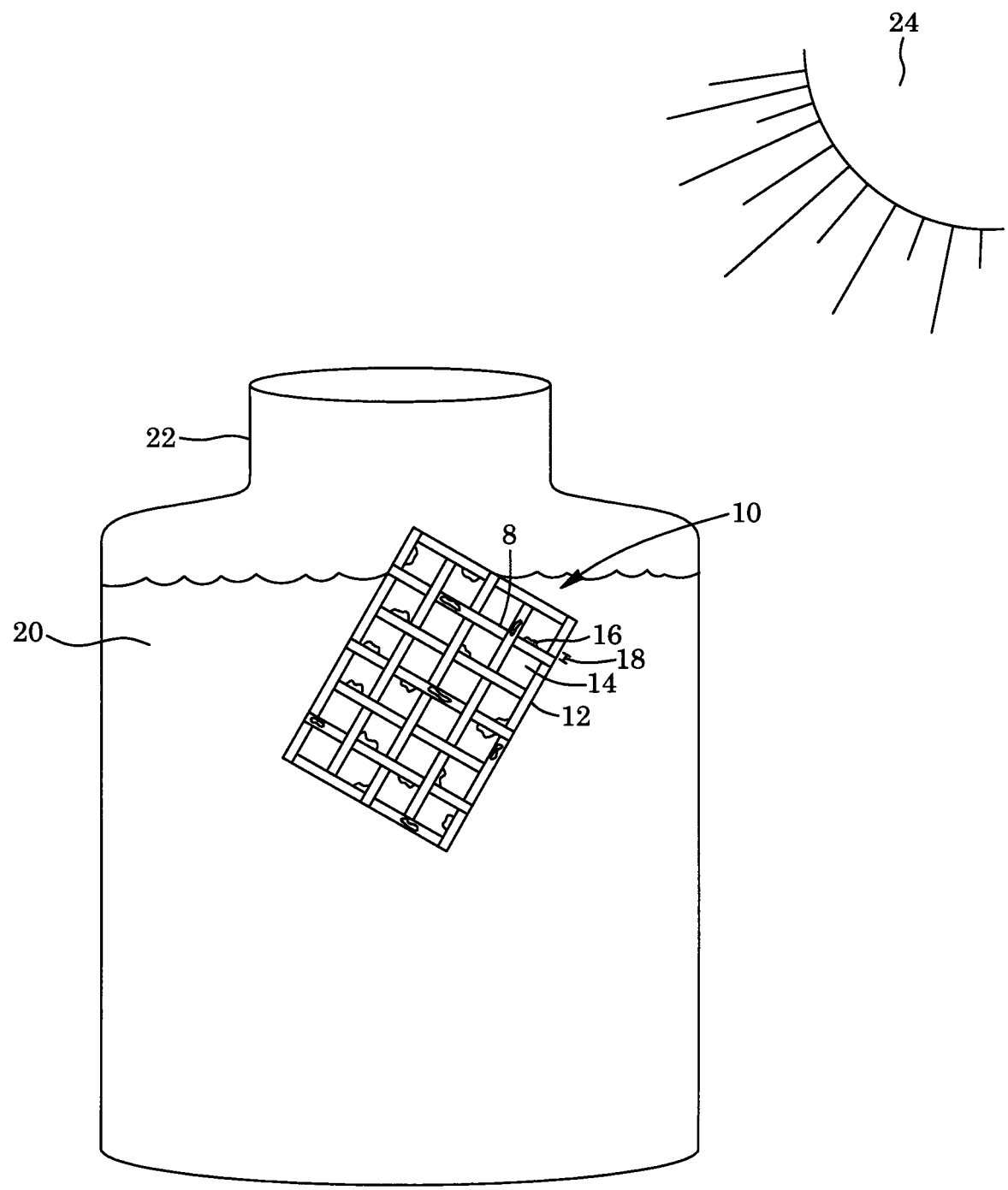
FIG. 2 is a schematic of a side view of a photoreactor which is a sheet for purifying water and other liquids.

In one embodiment, a photoreactor sheet, generally referred to as 10 is shown in FIG. 2. It includes a porous substrate 12, which is preferably porous glass, with interstitial spaces 14 and a continuous or discontinuous film 16 on the glass fibers 8 of the substrate 12. The film 16 has a thickness 18 of up to about 5 microns. The film 16 is low iron oxide, or substantially iron oxide free, iron-doped titanium dioxide and preferably contains about 0.5 atomic % iron. This embodiment is suitable for placing in water 20 in a drinking bottle 22 and exposing it to visible light 24, which can be sunlight or ambient lighting, with no requirement for the ultraviolet wavelengths of the spectrum.

Figure 3:
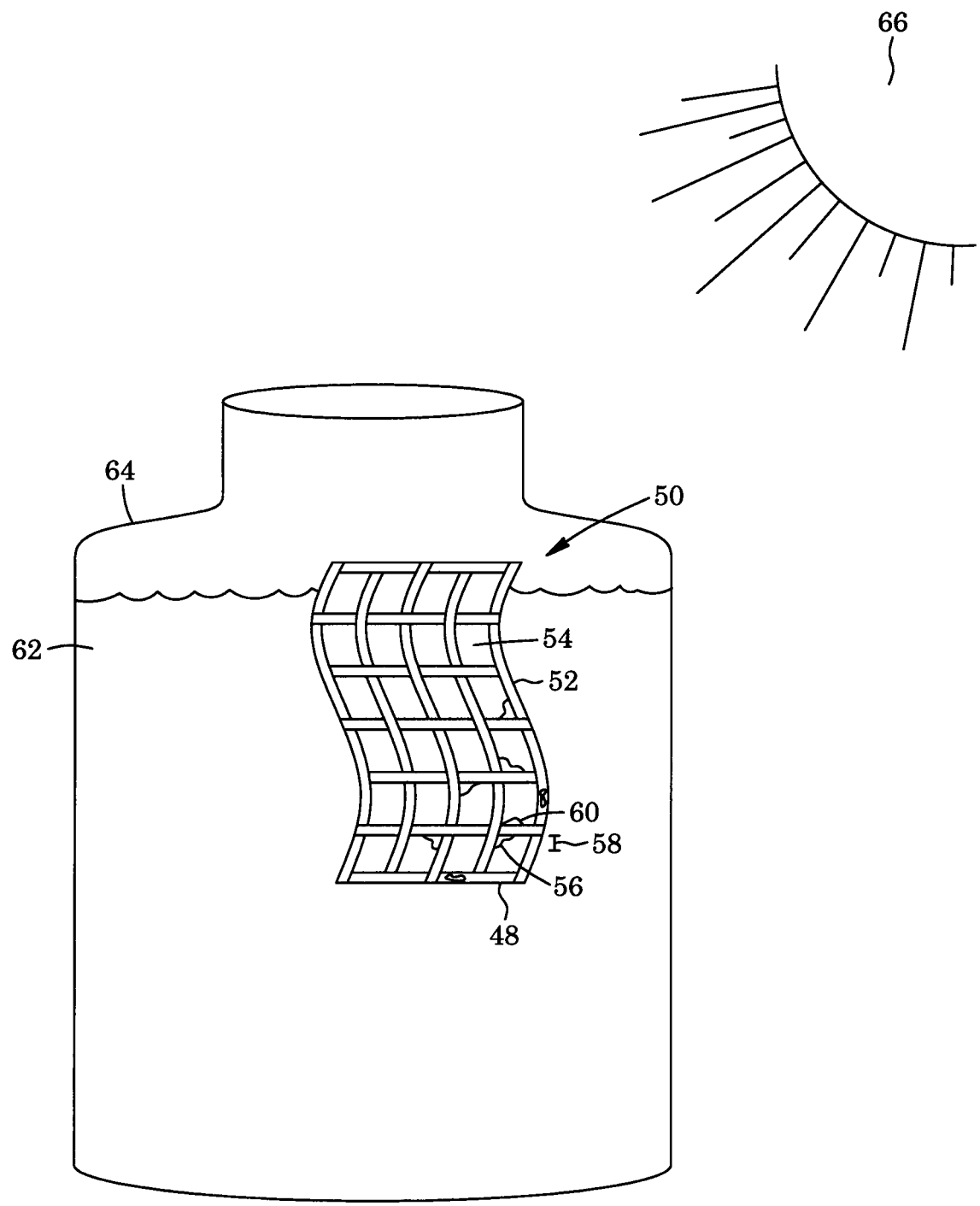
FIG. 3 is a schematic of a side view of a photoreactor which is a sheet for providing potable water.

In another embodiment, shown in FIG. 3, a photoreactor sheet, generally referred to as 50 includes a substrate 52 which is fiberglass fabric. It is flexible and can therefore be shaped in a wide range of shapes. The fiberglass fabric has interstitial spaces 54 and a continuous or discontinuous film 56 on the fiberglass threads 48. The film 56 has a thickness 58 of up to about 5 microns. The film 56 is low iron oxide, or substantially iron oxide free, iron-doped titanium dioxide and preferably contains about 0.5 atomic % iron. The film 56 can be seen to be nanocrystals 60. This embodiment is suitable for placing in water 62 in a drinking bottle 64 and exposing it to visible light 66, which may be sunlight or artificial lighting.

Figure 4:
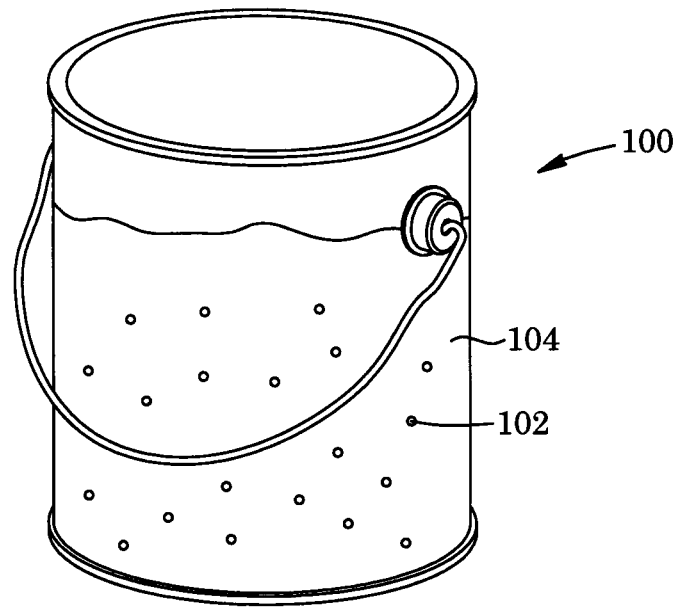
FIG. 4 is a schematic of a photoreactor paint.

In another embodiment, shown in FIG. 4, a photoreactor paint, generally referred to as 100 includes low iron oxide, or substantially iron oxide free, iron-doped titanium dioxide nanocrystals 102 in a paint formulation 104. The concentration of nanocrystals 102 was about 100,000 ppm to about 500,000 ppm, to provide a coverage of about 1 gram of nanocrystal 102 per 20 cm×20 cm. This was effective in providing a surface that, when exposed to visible light, could be cleaned by wiping with water, or in a higher humidity environment, simply wiping with a cloth.

Figure 5:
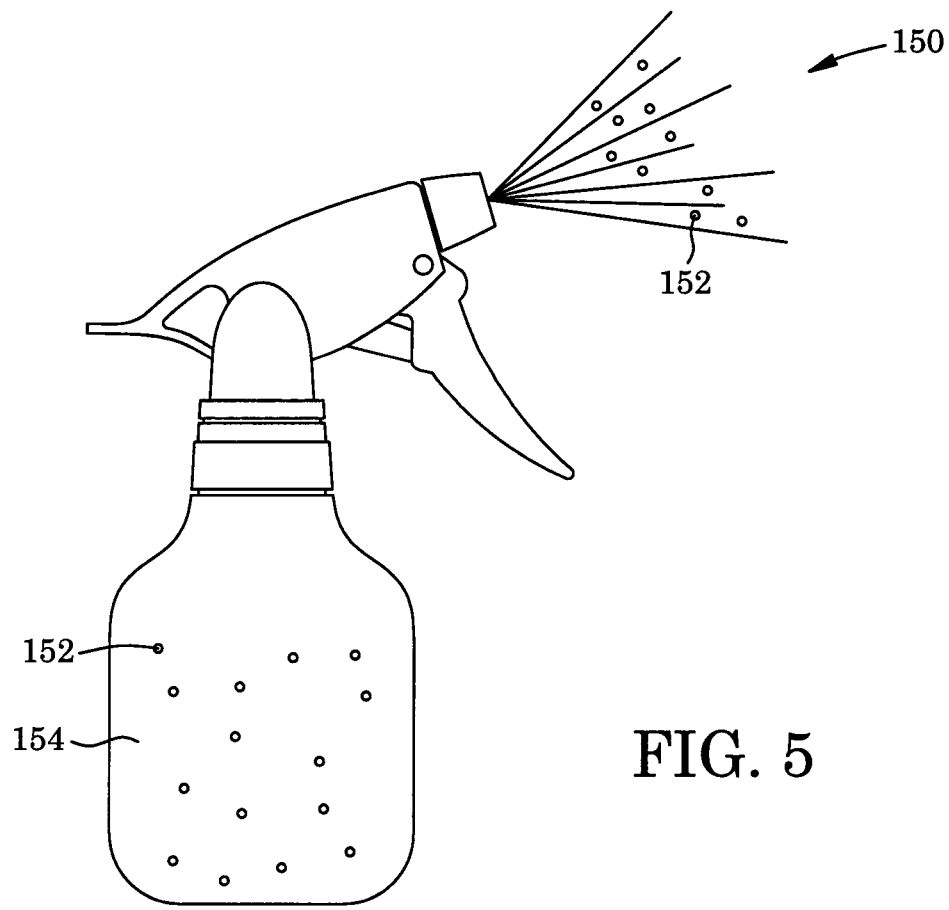
FIG. 5 is a schematic of a side view of a photoreactor spray.

In another embodiment, shown in FIG. 5, a photoreactor spray, generally referred to as 150 includes low iron oxide, or substantially iron oxide free, iron-doped titanium dioxide nanocrystals 152 in an aqueous formulation 154. The concentration of nanocrystals 152 was about 100,000 ppm to about 500,000 ppm. This was effective, when exposed to visible light, in treating fruits and vegetables to reduce microbial load, including but not limited to fungus and bacteria. This was also effective, when exposed to visible light, in reducing or eliminating mildew, for example, in showers and kitchens. The visible light was sunlight or ambient indoor lighting.

Figure 6:
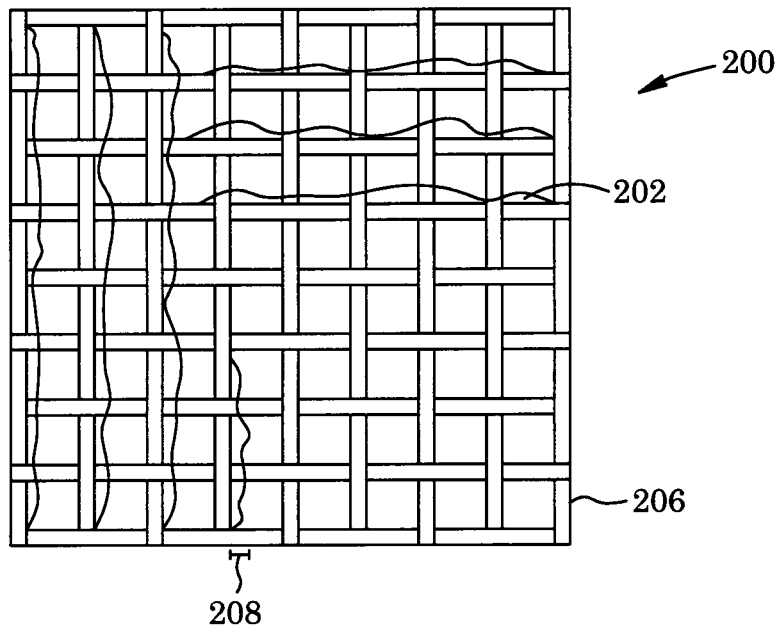
FIG. 6 is schematic of a photoreactor cloth.

In another embodiment, shown in FIG. 6, a photoreactor cloth, generally referred to as 200 includes a continuous or discontinuous film 202 of low iron oxide, iron-doped titanium dioxide or substantially iron oxide free iron-doped titanium dioxide on a cloth 206. The cloth 206 may be a fiberglass cloth, which can be as thin as 0.01 mm and as thick as 3, 4 or 5 millimeters thick. The continuous or discontinuous film 202 has a thickness 208 of up to about 3 millimeters with the higher limit being one that would allow the cloth 206 to be flexible. The low iron oxide, or substantially iron oxide free, iron-doped titanium dioxide preferably contains about 0.5 atomic % iron but can range from about 0.25 atomic % to about 0.75 atomic %. The photoreactor cloth 200 was used to clean a moist surface.

Figure 7:
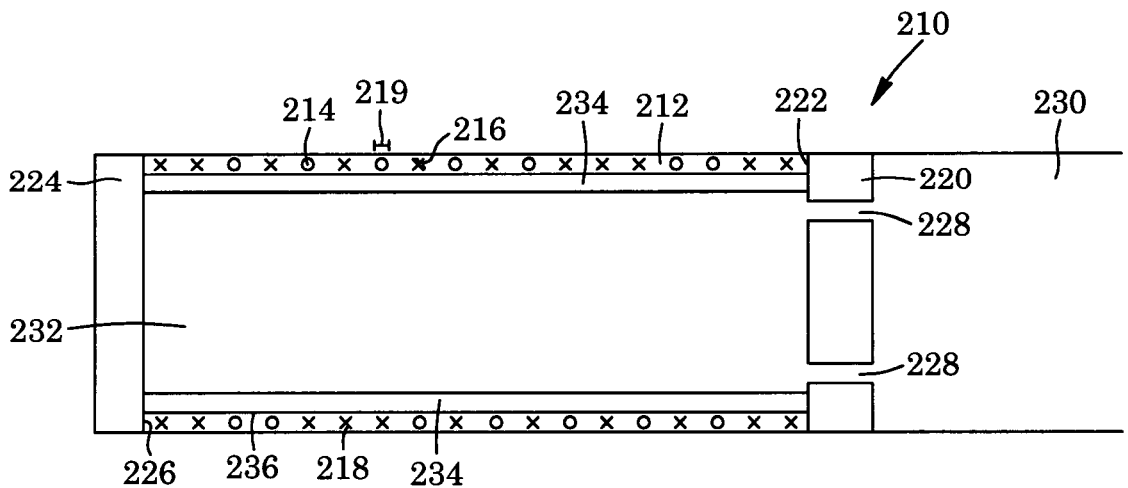
FIG. 7 is a schematic of a medial sectional view of a photoreactor apparatus for cleaning a flow of air.

In another embodiment, shown in FIG. 7, a photoreactor apparatus, generally referred to as 210, is provided. The photoreactor apparatus 210 has a porous glass tube 212, which is preferably fiberglass fabric with interstitial spaces 214 between the threads 216 of the tube 212 and a film 218 on the threads 216. The film 218 has a thickness 219 of up to about 5 microns. The film 218 is low iron oxide, or substantially iron oxide free, iron-doped titanium dioxide and preferably contains about 0.5 atomic % iron. In the preferred embodiment, the film 218 is nanocrystals of the low or substantially iron oxide free, iron-doped titanium dioxide. A cap 220 is affixed to a first end 222 of the tube 212 and a plate 224 is affixed on to a second end 226 of the tube 212. The cap 220 has a plurality of apertures 228 that extend between an air duct 230 and the bore 232 of the tube 212. The air in the air duct is preferably moist air. If the ambient air is dry, a humidifier can be added upstream of the bore 232 of the tube 212. Extending between and attached to the cap 220 and the plate 224 are support rods 234. The support rods 234 maintain the tube shape. The support rods 234 are located in the bore 232 of the tube 212 and press against the inner wall 236 of the tube 212. The support rods 234, the cap 22 and the plate 224 form a frame. The shape of the porous glass tube is dictated by the arrangement of the support rods 234 and may be, for example, but not limited to, round, square, octagonal, hexagonal, and elliptical. This embodiment is for cleaning air.

Figure 8:
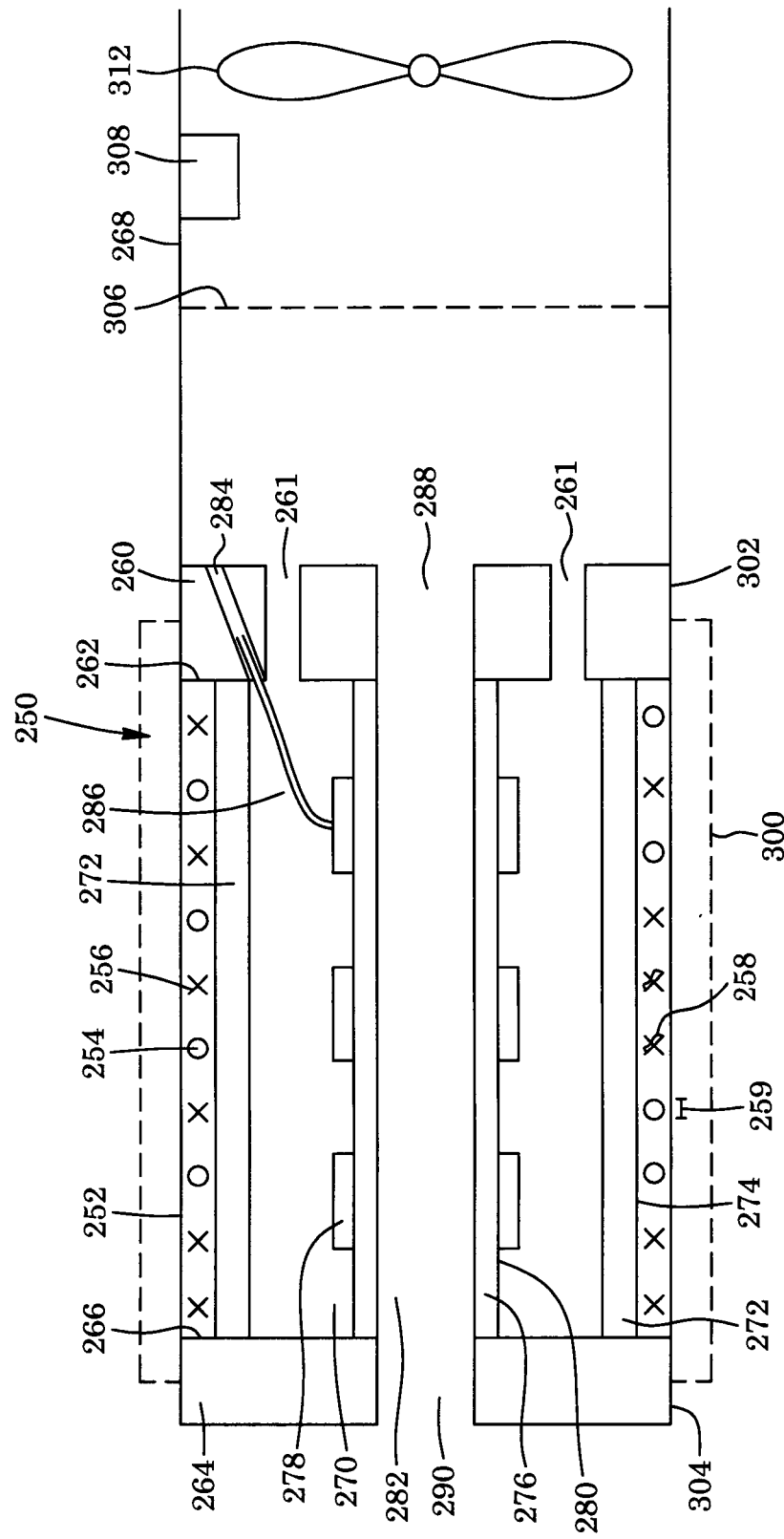
FIG. 8 is a schematic of a medial sectional view of an alternative embodiment of the photoreactor apparatus of FIG. 6.

In another embodiment shown in FIG. 8, a photoreactor apparatus, generally referred to as 250, is provided. This embodiment is for cleaning air. The photoreactor apparatus 250 has a porous glass tube 252, which is preferably fiberglass fabric with interstitial spaces 254 between the threads 256 of the tube 252 and a continuous or discontinuous film 258 on the threads 256. The film 258 has a thickness 259 of up to about 5 microns. The film 258 is low iron oxide, or substantially iron oxide free, iron-doped titanium dioxide and preferably contains about 0.5 atomic % iron. In the preferred embodiment, the film 258 is discontinuous and is nanocrystals of low iron oxide, iron-doped titanium dioxide or substantially iron oxide free iron-doped titanium dioxide. A cap 260 is affixed to a first end 262 of the tube 252 and a plate 264 is affixed on to a second end 266 of the tube 252. The cap 260 has a plurality of apertures 261 that extend between an air duct 268 and the bore 270 of the tube 252. The air in the air duct is preferably moist air. Extending between and attached to the cap 260 and the plate 264 are support rods 272. The support rods 272 maintain the tube shape. The support rods 272 are located in the bore 270 of the tube 252 and press against the inner wall 274 of the tube 252. An inner tube 276 is centrally located in the bore 272 and extends between and is attached to the cap 260 and the plate 264. The inner tube 276 has a plurality of light emitting diodes (LEDs) 278 on the outer surface 280 and an inner bore 282. A power aperture 284 extends through the cap 260 and carries a power line 286 to the LEDs 278. The LEDs 278 may be 100 watts each and there may be 12 LEDs 278 in a photoreactor 250 that is 25 cm long and 22 in diameter. The inner bore 282 is proportional to the size of the LEDs 278. For example, the area of the LEDs 278 may be about 50×50 mm$^2$. The diameter of the inner bore 282 would then be about 25 mm. The porous tube 252 is about 1 cm larger in diameter than the inner tube 276. The inner bore 282 is in fluid communication with a cap central aperture 288 and a plate central aperture 290. This allows for air to flow through the inner tube 276 to cool the photoreactor apparatus 250. The inner tube 276 is preferably aluminum. The shape of the porous glass tube 252 is dictated by the arrangement of the support rods 272 and may be, for example, but not limited to, round, square, octagonal, hexagonal, and elliptical. In one embodiment, the apparatus 250 is 25 cm long and 22 cm in diameter.

An outer protective mesh 300 surrounds at least the tube 252 of the photoreactor apparatus 250. It is preferably affixed to the outer circumference 302 of the cap 260 and the outer circumference 304 of the plate 264. A prefilter 306 may be placed upstream from the photoreactor apparatus 250. Additionally, a humidifier 308 may be placed upstream of the photoreactor apparatus to provide moisture to the air duct 268 which feeds pressurized air from an air pressurizer 312, which may be an air compressor, a fan or a pump, to the cap apertures 262. These components are also included in the photoreactor apparatus shown in FIGS. 7 and 10.

Figure 9:
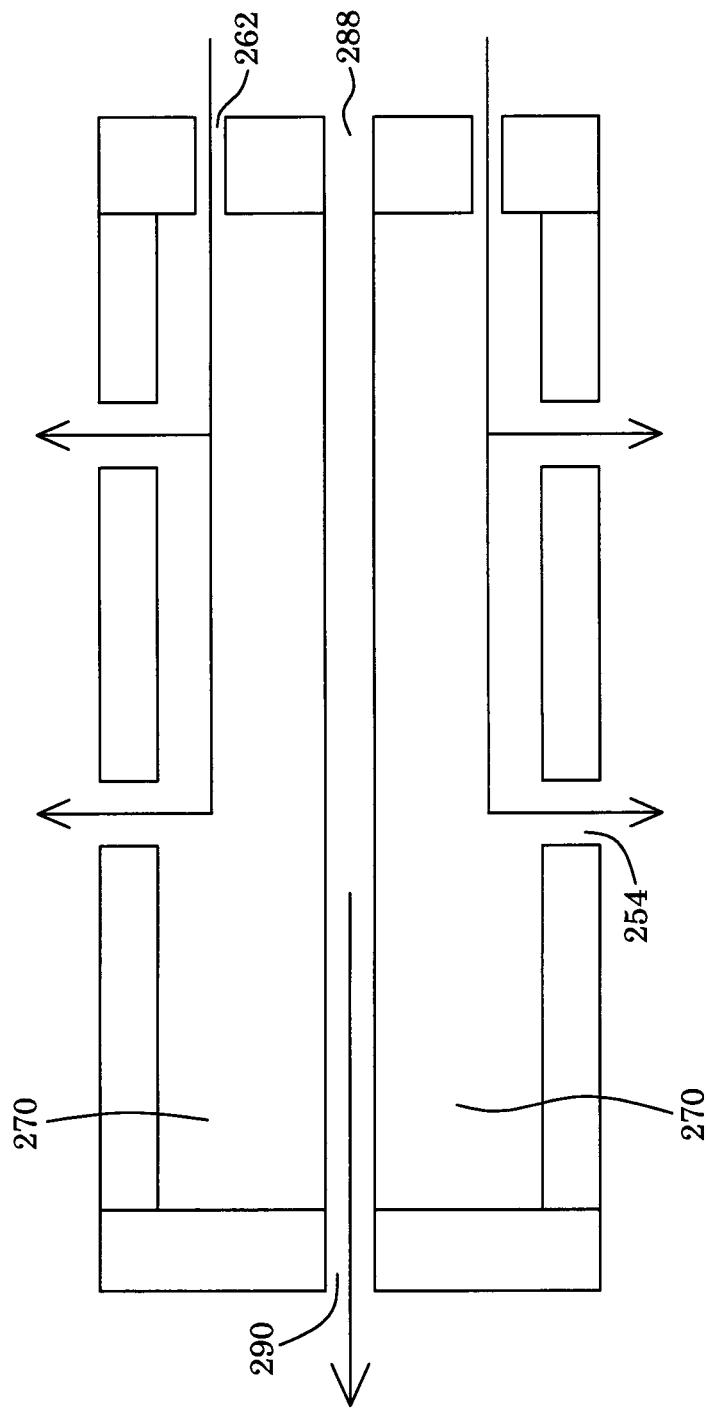
FIG. 9 is a simplified schematic showing the air flow pattern through the embodiments of FIGS. 7, 8 and 10.

As shown in FIG. 9, air is blown under pressure through the plurality of apertures 262 into the bore 270 and is forced out through the interstitial spaces 254, taking oxidants (oxidizing radicals) produced by the water and oxygen in air, hydroxyl ions by electrolysis and nanocrystals 258. The air flow is the same for the embodiments shown in FIGS. 7 and 10. The air is cleaned by the oxidants produced by the nanocrystals which are described in WO2018064747. A stack or bundle of the photoreactors 250 that is about meter long and 22 cm in diameter uses about 3.2 kilowatts to power the LEDs. A stack or bundle of the photoreactors is flexible in size due to the modularity of the design thus using power of a range of kilowatts for cleaning purposes. A plurality of the photoreactors 250 can be placed in an air conditioning or air ventilation system.

Figure 10:
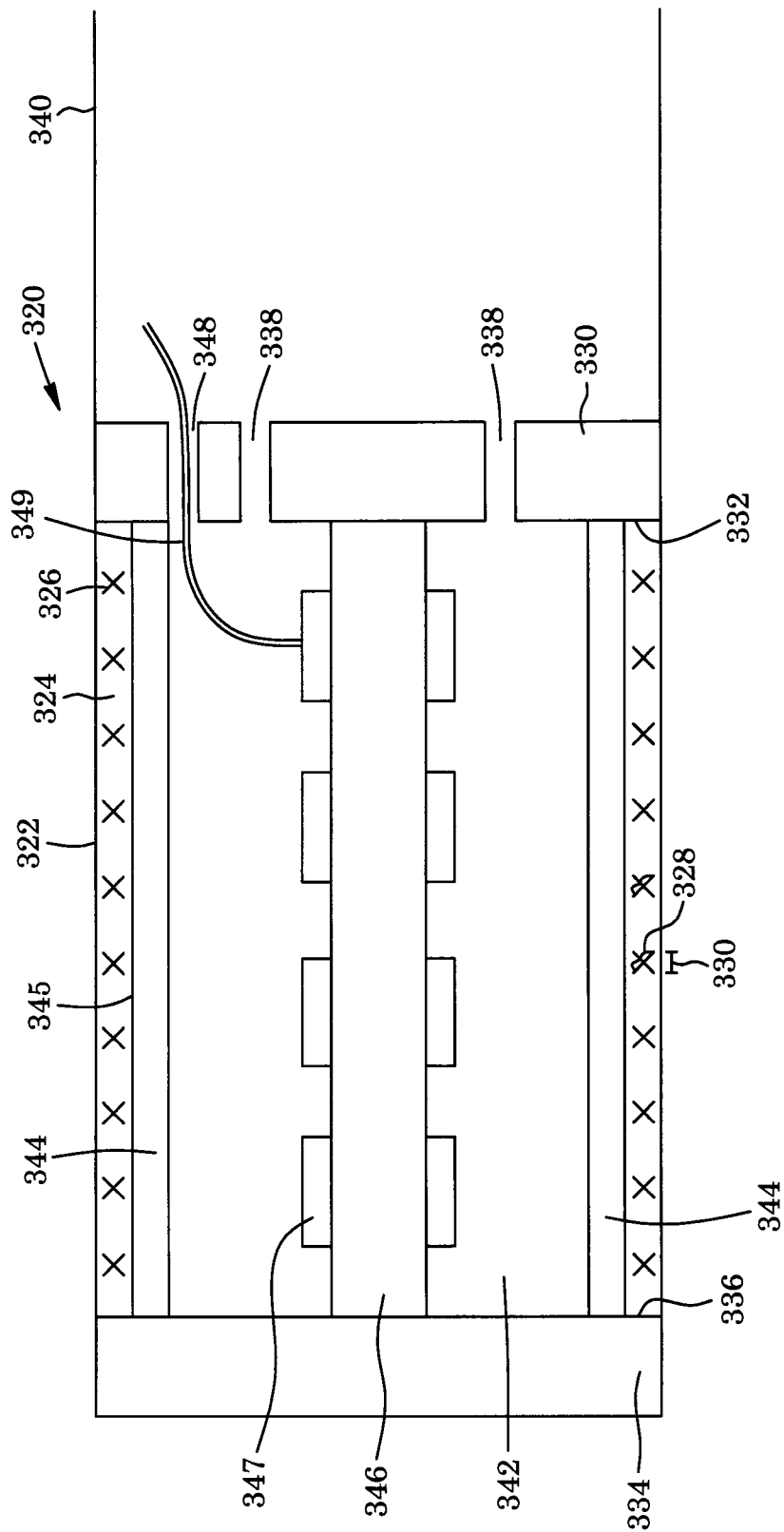
FIG. 10 is a schematic of a medial sectional view of another alternative embodiment of the photoreactor apparatus of FIG. 7.

In another embodiment, shown in FIG. 10, a photoreactor apparatus, generally referred to as 320, is provided. The photoreactor apparatus 320 has a porous glass tube 322, which is preferably fiberglass fabric with interstitial spaces 324 between the threads 326 of the tube 322 and a film 328 on the threads 326. The film 326 has a thickness 330 of up to about 5 microns. The film 328 is low iron oxide, iron-doped titanium dioxide or substantially iron oxide free, iron-doped titanium dioxide and preferably contains about 0.5 atomic % iron. In the preferred embodiment, the film 328 is nanocrystals of the low or substantially iron oxide free, iron-doped titanium dioxide. A cap 330 is affixed to a first end 332 of the tube 322 and a plate 334 is affixed on to a second end 336 of the tube 322. The cap 330 has a plurality of apertures 338 that extend between an air duct 340 and the bore 342 of the tube 322. Extending between and attached to the cap 330 and the plate 334 are support rods 344. The support rods 344 maintain the tube shape. The support rods 344 are located in the bore 342 of the tube 322 and press against the inner wall 345 of the tube 322. A support 346 is centrally located in the bore 342 and extends between and is attached to the cap 330 and the plate 334. The support 346 supports a plurality of light emitting diodes (LEDs) 347. A power aperture 348 extends through the cap 330 and carries a power line 349 to the LEDs 347. The shape of the porous glass tube 322 is dictated by the arrangement of the support rods 344 and may be, for example, but not limited to, round, square, octagonal, hexagonal, and elliptical. The air flow is as described for FIG. 9.

In an exemplary example, the photoreactor apparatus 250, 320 is used to scrub air from greenhouses, more specifically, cannabis growing greenhouses. The scrubbing reduces or eliminates volatile organic compounds, thus can be used to control odours from the greenhouses.

In another exemplary example, the photoreactor apparatus 250, 320 is used to scrub air in air conditioners or air ventilation systems. The scrubbing reduces or eliminate volatile organic compounds and microbes.

In another exemplary example, the photoreactor apparatus 250, 320 is used to scrub air from oil refineries. The scrubbing reduces or eliminates volatile organic compounds which reduces odours and reduces dangerous volatile chemicals from the environment.

In another exemplary example, the photoreactor apparatus 250, 320 is used to scrub air in farm buildings. The scrubbing reduces or eliminate volatile organic compounds and microbes.

An alternative embodiment, shown in FIG. 11, is designed for cleaning water contaminated with organic material and organic compounds. The photoreactor apparatus 350 has a porous glass tube 352, which is preferably fiberglass fabric with interstitial spaces 354 between the threads 356 of the tube 352 and a continuous or discontinuous film 358. The film 358 has a thickness 359 of up to about 5 microns on the threads 356. The film 358 is low iron oxide, or substantially iron oxide free, iron-doped titanium dioxide and preferably contains about 0.5 atomic % iron. In the preferred embodiment, the film 358 is discontinuous and is nanocrystals of low iron oxide, or substantially iron oxide free, iron-doped titanium dioxide. A cap 360 is affixed to a first end 362 of the tube 352 and a plate 364 is affixed on to a second end 366 of the tube 352. The cap 360 has a plurality of apertures 367 that extend between an air source 368 and the bore 370 of the tube 352. Extending between and attached to the cap 360 and the plate 364 are support rods 372. The support rods 372 maintain the tube shape. The support rods 372 are located in the bore 370 of the tube 352 and press against the inner wall 374 of the tube 352. An inner tube 376 is centrally located in the bore 370 and extends between and is attached to the cap 360 and the plate 364. The inner tube 376 has a plurality of light emitting diodes (LEDs) 378 on the outer surface 380 and an inner bore 382. The inner tube 376 is preferably aluminum. A power aperture 384 extends through the cap 360 and carries a power line 386 to the LEDs 378. The inner bore 382 is in fluid communication with a cap central aperture 388 and a plate central aperture 390. This allows for liquid to flow through the inner tube 376 to cool the photoreactor apparatus 350. As an additional component, a glass tube 390 is located in the bore 370 of the tube 352. This glass tube 390 is functionalized with a continuous or discontinuous film 391 of low iron oxide, iron-doped titanium dioxide. A cap gasket 392 is located between a first end 394 of the glass tube 390 and the cap 360 and a plate gasket 396 is located between a second end 398 of the glass tube 390 and the plate 364. These provide a waterproof seal. The inner tube 376 is housed in the glass tube bore 400. The glass tube 390 protects the LEDs 378 from the liquid in the ambient environment 402.

An outer protective mesh 410 surrounds at least the tube 352 of the photoreactor apparatus 350. It is preferably affixed to the outer circumference 412 of the cap 360 and the outer circumference 414 of the plate 364. A prefilter 416 may be placed upstream from the photoreactor apparatus 350. The shape of the porous glass tube 352 is dictated by the arrangement of the support rods 372 and may be, for example, but not limited to, round, square, octagonal, hexagonal, and elliptical.

Figure 12:
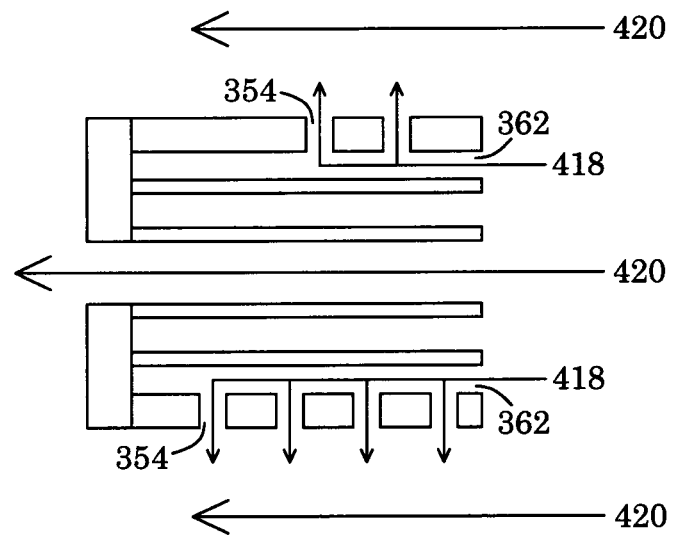
FIG. 12 is a simplified schematic showing the flow pattern of the apparatus of FIG. 11.

As shown in FIG. 12, humid air is blown 418, under force, through the plurality of apertures 362 into the bore 370 and is forced out through the interstitial spaces 354, taking oxidants (oxidizing radicals) produced by the air and nanocrystals 358. The liquid 420, which may be wastewater, and may have, as contaminants, organic compounds, small organic particulates, phosphates, organometals, and/or ammonia, is cleaned by the nanocrystals which are described in WO2018064747 as it flows over the photoreactor apparatus 350. The wastewater flows through the inner tube 376 to cool the apparatus. 350. This design was also used for cleaning air.

Figure 13:
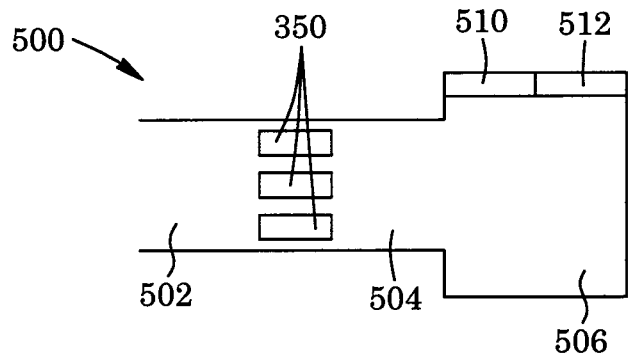
FIG. 13 is a schematic of a medial sectional view of an installation including the photoreactor apparatus for cleaning water.

As shown in FIG. 13, an installation, generally referred to as 500 has a plurality of photoreactor apparatuses 350. The photoreactor apparatuses can be stacked or bundled. The installation includes a wastewater/effluent supply line 502, which may be a pipe, a culvert or a ditch into which the photoreactor apparatuses 350 are located and a clean liquid line 504 downstream from the photoreactor apparatus 350. A bioreactor 506 is downstream from the clean liquid line 504 and includes a light source 510, which may be sunlight or an artificial light source and a carbon dioxide source 512, which may be air or may be carbon dioxide from the photoreactors 350. The bioreactor 506 contains phytoplankton. In use, the photoreactors 350 oxidize organic compounds, small organic particulates, organometals, ammonia and phosphorus and produces nitrates, nitrites, carbon dioxide and phosphates. The phytoplankton in the bioreactor 506 removes the nitrates, nitrites, carbon dioxide and phosphates. The phytoplankton are then harvested and are used as an organic fertilizer.

Figure 14:
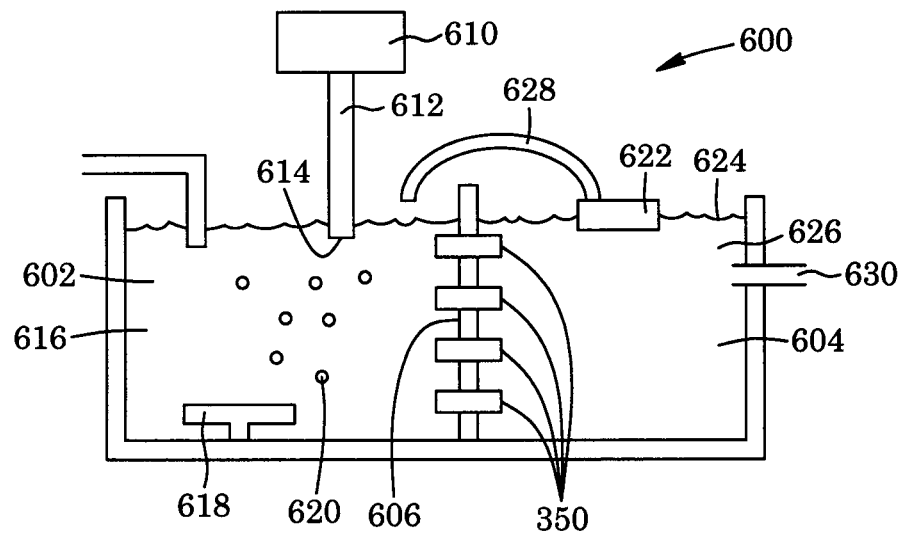
FIG. 14 is a schematic of a medial sectional view of an alternative embodiment of FIG. 13.

As shown in FIG. 14, another installation 600 includes a photoreactor pond 602 and a bioreactor 604 with a wall 606 therebetween. A plurality of photoreactors 350 are retained by the wall 606 and extend between the photoreactor pond 602 and the bioreactor 604. A source of compressed air 610, such as an air compressor provides a flow of air to an intake pipe 612. An outlet 614 on the intake pipe 612 is located in the wastewater 616 in the photoreactor pond 602. An air diffuser 618 is located in the photoreactor pond 602 to promote circulation of both the wastewater 616 and the air 620. A surface skimmer 622 is located in the bioreactor 604, proximate the surface 624 of the cleaned water 626. A pipe 628 is in fluid communication with the surface skimmer 622 and returns cleaned water 626 to the photoreactor pond 602 for further cleaning. An effluent pipe 630 is also located in the bioreactor 604 and is in fluid communication with the cleaned water 626. In use, the photoreactors 350 oxidize organic compounds, small organic particulates, organometals, ammonia and phosphorus and produces nitrates, nitrites, carbon dioxide and phosphates. The phytoplankton in the bioreactor 604 removes the nitrates, nitrites, carbon dioxide and phosphates. The phytoplankton are then harvested and are used as an organic fertilizer. A slurry of phytoplankton in cleaned water may be directly sprayed on the crops, or in cleaned water with a surfactant or the phytoplankton may be dried and then applied as a slurry with an aqueous solution which may or may not include a surfactant.

In alternative embodiments of FIGS. 1 to 14, the porous glass, the fiberglass fabric and the fiberglass cloth as disclosed are replaced with carbon fiber fabric.

In other alternative embodiments of FIGS. 1 to 14, the porous glass, the fiberglass fabric and the fiberglass cloth as disclosed are replaced with Kevlar fabric.

Figure 15:
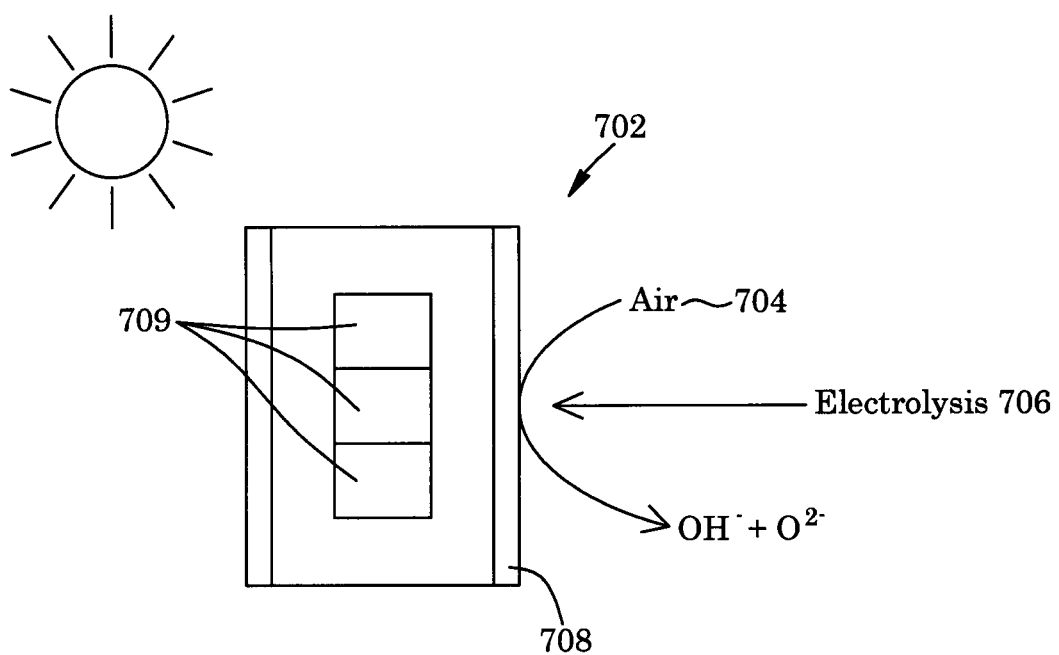
FIG. 15 is a schematic of an embodiment of an electro-visible light photo-chemical reactor.

As shown in FIG. 15, in another embodiment, an electro-visible light photo-chemical reactor, generally referred to as 702 is provided. It utilizes a combination of a flow of air 704, electrolysis 706, low iron oxide iron doped titanium dioxide particles 708 and light 709 to clean fluids. The low iron oxide, iron-doped titanium dioxide particles range in size from nanometers (individual single crystals) to hundreds of microns (aggregates of single crystals). Without the flow of air and the electrolysis, OH– and $O^{2-}$ ions become depleted in the wastewater being cleaned so the rate of wastewater degradation decrease. Adding air and electrolysis-generated OH– opens up the wastewater cleaning bottleneck to make superoxide and hydroxyl radicals. Rate of wastewater degradation increases. Without being bound to theory, the low iron oxide iron doped titanium dioxide produces electrons and holes when exposed to visible light. The electrons combine with Fe+3 in the low iron oxide iron doped titanium dioxide to form Fe+2 and the hole combines with Fe+3 to form Fe+4. The Fe+2 ion reacts with O2 to form superoxide, an oxidizing radical. The Fe+4 ion reacts with OH– ions to form the hydroxyl radical. By blowing air through the activated fiberglass cloth to provide O2 and by producing an electrolytic current passing through the activated fiberglass cloth to provide OH– ions, the bottleneck caused by insufficient radicals is overcome.

Figure 16:
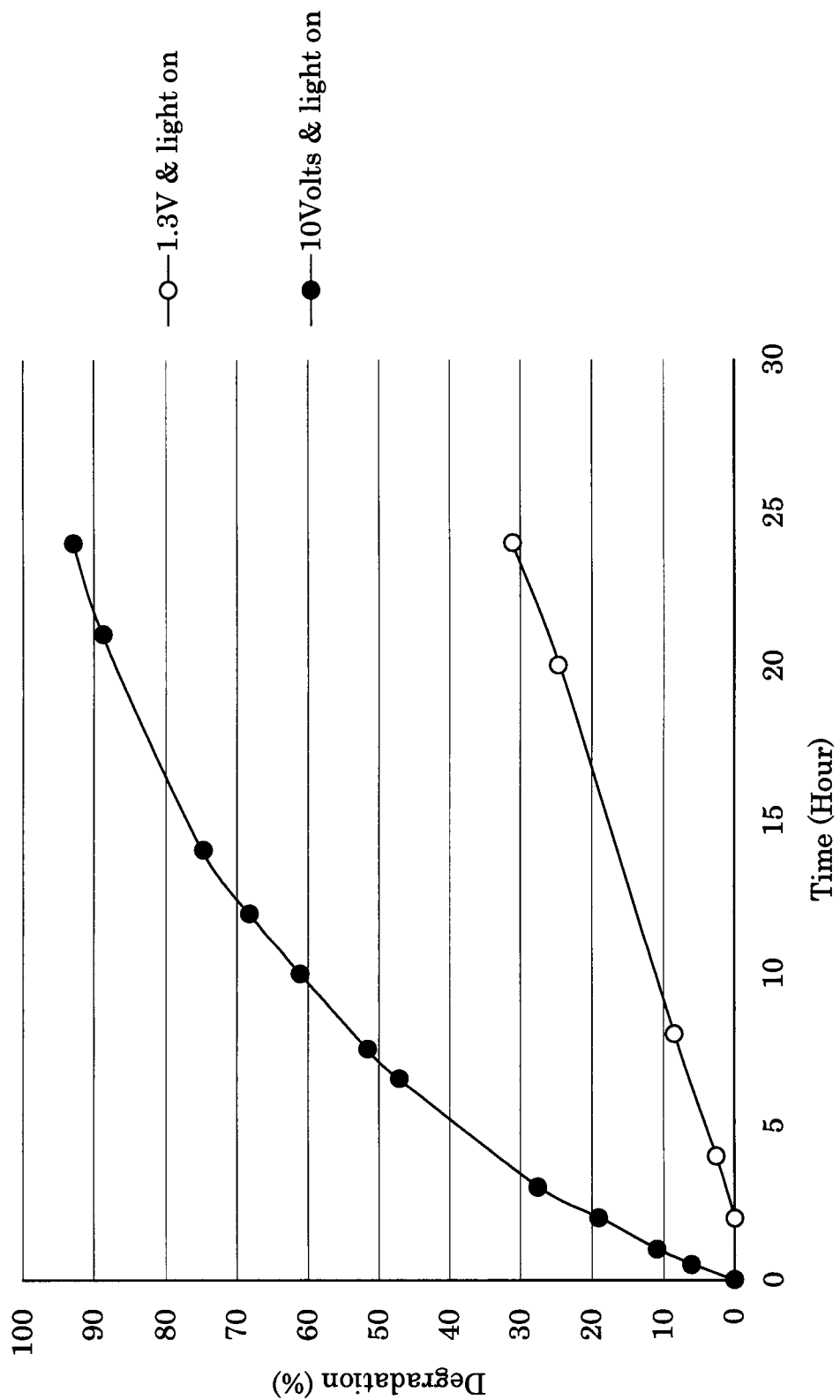
FIG. 16 is a graph showing cleaning of methyl orange with the electro-visible light photo-chemical reactor of FIG. 15.

As shown in FIG. 16, using the electro-visible light photo-chemical reactor 702 operating with 10 Volts of power to the electrolysis system and visible light LEDs leads to greater than 90% of waste (organic and ammonia) being cleaned within 24 hours. The photoreactor volume is about 1 liter and is used to clean about 20 liters of wastewater. This is cleaning 20 times faster than a bioreactor that is in common use today. Bioreactors are the size of the volume of water being cleaned and take 24 hours to clean 90% of the organic waste and none of the ammonia. The electro-visible light photo-chemical reactor also cleans or oxidizes ammonia producing nitrates and nitrites.

As shown in FIG. 17A, the core of the electro-visible light photo-chemical reactor 702 is a column of visible light LEDs 710. The visible light LEDs 710 are mounted on a base 712, which has an annular ring 714 for accepting the cathode 726 (see FIG. 17C). As shown in FIG. 17B, the column of LEDs 710 has air lines 712 around the LEDs 710, placed such that they do not interfere with the light path from them. A cover 716 has a first air inlet 718 and a second air inlet 720. The air lines 712 have a plurality of apertures 722. As shown in FIG. 17C, the cathode, generally referred to as 726 is a tubular metal screen or mesh 728 with a top 730 and a base 732. The top has an electrical connector 734. As shown in FIG. 17D, a low iron oxide, iron-doped titanium dioxide activated mesh 740, which is preferably a plurality of fiberglass sheets, extends between the top 730 and the base 712. The fibers of the outermost layer have gold deposited on them as a thin discontinuous layer about 80 to 100 nm thick prior to being activated with the low iron oxide, iron-doped titanium dioxide. The layer is a discontinuous layer to ensure that the low iron oxide, iron-doped titanium dioxide adheres to the fiber of the fiberglass mesh 740. Without being bound to theory, the gold converts a photon of light into a surface plasmon. The surface plasmon can travel many millimeters before decaying as heat. The heat reduces the bandgap of titanium dioxide further, thus allowing the titanium dioxide to absorb a larger range of wavelengths of light. Also, since the separation between the low iron oxide, iron-doped titanium dioxide particles is much less than 100 microns, rather than decaying as heat, some of the surface plasmons can be absorbed onto the low iron oxide, iron-doped titanium dioxide particles, transferring its energy to electrons and positive holes for the catalytic reactions for producing superoxide and hydroxyl radicals. In this manner, not only is there little or no light being lost from the system, the energy from light striking the gold is returned to the system. This therefore further increases the efficiency of cleaning.

As shown in FIG. 17E, the anode, generally referred to as 746 is a tubular metal screen or mesh 748 with a top 750 and a base 752. The top has an electrical connector 754. Struts 756 extend between the top 750 and the base 752 to support the electro-visible light photo-chemical reactor 702.

The assembled electro-visible light photo-chemical reactor 702 is shown in FIG. 18. A lid 760 has a first electrical connection 762 for an incoming power line 764, a second electrical connection 766 for an outgoing power line 768, a first air inlet 780 connected to an incoming air line 782 and a second air outlet 784 connected to another incoming air line 786. The lid 760 is connected to outer struts 788, which extend from the lid 760 to the bottom 790. A heater 792 is attached to the bottom 790 to heat the electro-visible light photo-chemical reactor 702. Without being bound to theory, heat reduces the bandgap, thus allowing a broader range of wavelengths of light to be absorbed by the low iron oxide iron-doped titanium dioxide. Heat allows the low iron oxide iron-doped titanium dioxide to absorb UV, blue, green and yellow, which enables the low iron oxide iron-doped titanium dioxide to capture more of the energy from light sources like the sun. Absorbing more of the light spectrum increases the efficiency of the system and thus increases the cleaning power of the crystals.

The total volume of the electro-visible light photo-chemical reactor 702 can be scaled. The area ratio between the cathode 726 and the anode 746 is variable, however, in general the ratio is preferably about 1:1, noting that the cathode area is slightly smaller than the anode area because of the fiberglass sheets in between, or if arranged with the anode on the inside and the cathode on the outside, the anode area is slightly smaller than the anode area. As the size of the electro-visible light photo-chemical reactor 702 increases the ratio approaches the theoretical limit of 1:1 where the area of the anode equals the area of the cathode.

Currently, twelve 100-watt LED lamps are used in a one liter electro-visible light photo-chemical reactor 702 to provide 1,220 watts of lamp power. This is directly scalable.

As shown in FIG. 19, the efficiency is higher when the cathode is on the air releasing side of the low iron oxide, iron-doped titanium dioxide activated mesh as compared to when the anode is on the air releasing side of the low iron oxide, iron-doped titanium dioxide activated mesh (forward versus reverse).

As shown in FIG. 20, a planar electro-visible light photochemical reactor, generally referred to as 800 has a plurality of visible light LEDs 810 which are arranged to illuminate a low iron oxide, iron-doped titanium dioxide activated mesh 840, which is preferably a plurality of activated fiberglass sheets. In one embodiment, the fibers of the outermost layer have gold deposited on them as a thin discontinuous layer about 80 to 100 nm thick prior to being activated with the low iron oxide, iron-doped titanium dioxide. The layer is a discontinuous layer to ensure that the low iron oxide, iron-doped titanium dioxide adheres to the fiber of the fiberglass mesh 840. Air lines 812 are preferably at the bottom of the electro-visible light photo-chemical reactor 800 and include a plurality of apertures 822. An air inlet 818 is located along the air line 812. A cathode 826 is a metal (or electrically conductive) screen or mesh. It has an electrical connector 834. An anode 846 is a metal (or electrically conductive) screen or mesh. It has an electrical connector 854. Struts 856 extend between the top 850 and the base 852 to provide a frame which supports the electro-visible light photo-chemical reactor 800.

In an alternative embodiment, the outermost layer of the fibers only has gold deposited on it, and does not have the low iron oxide, iron-doped titanium dioxide. It is pressed to the penultimate layer such that the surface plasmons can be absorbed by the low iron oxide iron-doped titanium dioxide.

As would be known to one skilled in the art, the visible light photoreactor of the present technology does not require ultraviolet light in order to efficiently decompose organic waste in a fluid, however, this does not preclude the inclusion of light in the ultraviolet wavelengths.

While the technology has been described in detail, such a description is to be considered as exemplary and not restrictive in character and is to be understood that it is the presently preferred embodiments of the present technology and is thus representative of the subject matter which is broadly contemplated by the present technology, and that all changes and modifications that come within the spirit of the disclosure are desired to be protected.

The invention claimed is:

1. A non-biological, visible light photoreactor, the photoreactor comprising: a tube comprising a plurality of porous glass, carbon fiber or poly-paraphenylene terephthalamide filter layers, of which an outermost filter layer includes a discontinuous layer of gold, each filter layer including fibers and interstitial spaces between the fibers, wherein there is an iron-doped titanium dioxide film on the fibers, the film including a surface that is substantially iron oxide free, the tube including an inner wall that defines a bore; and a frame, the frame comprising a cap, a plate and support members, the support members attached to the cap and the plate and extending therebetween, the support members abutting the inner wall of the tube.

2. The photoreactor of claim 1, wherein the porous glass, carbon fiber or poly-paraphenylene terephthalamide filter layers are retained by the frame.

3. The photoreactor of claim 2, further comprising a plurality of visible light emitting diodes housed in the frame.

4. The photoreactor of claim 3, wherein the film includes about 0.1 atomic percent iron to about 2.0 atomic percent iron.

5. The photoreactor of claim 4, further comprising: an anode which is a metal mesh; a cathode which is a metal mesh, the anode and the cathode sandwiching the filter layers of the tube; and electrical connectors for the anode and the cathode.

6. The photoreactor of claim 5, further comprising: at least one air line which include apertures, the air line located proximate the filter layers; and an air inlet in fluid communication with the air line.

7. The photoreactor of claim 6, further comprising a heater which is proximate the cap or the plate.

8. The photoreactor of claim 7, wherein the plurality of visible light emitting diodes are housed in the bore within the frame.

9. A method of non-biologically reducing organic waste in a fluid, the method comprising:
   i) selecting a non-biological, visible light photoreactor, the photoreactor including: a tube comprising a plurality of porous glass, carbon fiber or poly-paraphenylene terephthalamide filter layers, of which an outermost filter layer includes a discontinuous layer of gold, each filter layer including fibers and interstitial spaces between the fibers, wherein there is an iron-doped titanium dioxide film on the fibers, the film containing about 0.5 atomic percent iron and including a surface which is substantially iron oxide free; the tube including an inner wall that defines a bore; and a frame, the frame comprising a cap, a plate and support members, the support members attached to the cap and the plate and extending therebetween, the support members abutting the inner wall of the tube,
   ii) exposing the filter to visible light; and
   iii) concomitantly exposing the fluid to the filter layers, thereby reducing organic waste in the fluid.

10. The method of claim 9, wherein the exposing the fluid is flowing the fluid through the filter layers.

11. The method of claim 10, wherein the fluid is air.

12. The method of claim 10, wherein the fluid is a liquid.

13. The method of claim 12, wherein the liquid is water.

14. A non-biological, visible light photoreactor, the photoreactor comprising: a porous glass, carbon fiber or poly-paraphenylene terephthalamide porous tube which defines a bore and includes fibers and interstitial spaces between the fibers; an iron-doped titanium dioxide film on the fibers, the film including a surface which is substantially iron oxide free; a cap at a first end of the tube; a plate at a second end of the tube; a plurality of support members, the support members attached to the cap and the plate and extending therebetween; a plurality of visible light emitting diodes housed in the bore; an anode which is a metal mesh tube; and a cathode which is a metal mesh tube, the anode and the cathode extending between the cap and the plate and sandwiching the porous tube the tube including an inner wall that defines a bore; and a frame, the frame comprising a cap, a plate and support members, the support members attached to the cap and the plate and extending therebetween, the support members abutting the inner wall of the tube.

15. The photoreactor claim 14, further comprising a coating of gold on the porous tube.

16. The photoreactor of claim 15, wherein the coating of gold is a discontinuous layer.

* * * * *

UNITED STATES PATENT AND TRADEMARK OFFICE
CERTIFICATE OF CORRECTION

PATENT NO. : 11,975,990 B2
APPLICATION NO. : 17/428259
DATED : May 7, 2024
INVENTOR(S) : Rodney Herring It is certified that error appears in the above-identified patent and that said Letters Patent is hereby corrected as shown below:

In the Claims

Column 16, Line 12 Claim 14 should be amended to read as follows:
14. A non-biological, visible light photoreactor, the photoreactor comprising: a porous glass, carbon fiber or poly-paraphenylene terephthalamide porous tube and having an inner wall which defines a bore and includes fibers and interstitial spaces between the fibers; an iron-doped titanium dioxide film on the fibers, the film including a surface which is substantially iron oxide free; a frame, the frame comprising a cap at a first end of the tube, a plate at a second end of the tube, and support members, the support members attached to the cap and the plate and extending therebetween, the support members abutting the inner wall of the tube; a plurality of visible light emitting diodes housed in the bore; an anode which is a metal mesh tube; and a cathode which is a metal mesh tube, the anode and the cathode extending between the cap and the plate and sandwiching the porous tube.

Signed and Sealed this
Fourth Day of June, 2024

Katherine Kelly Vidal
*Director of the United States Patent and Trademark Office*